US008188046B2

(12) United States Patent
Cao

(10) Patent No.: US 8,188,046 B2
(45) Date of Patent: May 29, 2012

(54) AMYLOID BETA PEPTIDES AND METHODS OF USE

(75) Inventor: Chuanhai Cao, Tampa, FL (US)

(73) Assignee: University of South Florida, Tampa, FL (US)

( * ) Notice: Subject to any disclaimer, the term of this patent is extended or adjusted under 35 U.S.C. 154(b) by 128 days.

(21) Appl. No.: 12/444,647

(22) PCT Filed: Oct. 12, 2007

(86) PCT No.: PCT/US2007/081235
§ 371 (c)(1),
(2), (4) Date: Oct. 15, 2009

(87) PCT Pub. No.: WO2008/070284
PCT Pub. Date: Jun. 12, 2008

(65) Prior Publication Data

US 2010/0172879 A1 Jul. 8, 2010

Related U.S. Application Data

(60) Provisional application No. 60/898,080, filed on Jan. 29, 2007, provisional application No. 60/851,966, filed on Oct. 16, 2006.

(51) Int. Cl.

| | |
|---|---|
| ***A61K 38/17*** | (2006.01) |
| ***A61P 25/28*** | (2006.01) |
| ***C07H 21/00*** | (2006.01) |
| ***C07K 14/435*** | (2006.01) |

(52) U.S. Cl. ..................... 514/17.8; 514/21.3; 536/23.5; 530/324

(58) Field of Classification Search ........................ None
See application file for complete search history.

(56) References Cited

U.S. PATENT DOCUMENTS

| | | | | |
|---|---|---|---|---|
| 5,387,742 | A | 2/1995 | Cordell | |
| 5,854,204 | A | 12/1998 | Findeis et al. | |
| 6,455,308 | B1 | 9/2002 | Freier | |
| 6,670,399 | B2 | 12/2003 | Green et al. | |
| 6,761,888 | B1 | 7/2004 | Schenk | |
| 6,875,434 | B1 | 4/2005 | Schenk | |
| 6,890,535 | B1 | 5/2005 | Schenk | |
| 6,905,686 | B1 | 6/2005 | Schenk | |
| 6,972,127 | B2 | 12/2005 | Schenk | |
| 7,060,671 | B1 | 6/2006 | Stott | |
| 7,135,181 | B2 | 11/2006 | Jensen et al. | |
| 7,175,828 | B2 | 2/2007 | Findeis et al. | |
| 7,179,892 | B2 | 2/2007 | Basi et al. | |
| 7,189,819 | B2 | 3/2007 | Basi et al. | |
| 7,256,273 | B2 | 8/2007 | Basi et al. | |
| 7,618,944 | B2 * | 11/2009 | Breitenkamp et al. | 514/1.1 |
| 2003/0086938 | A1 | 5/2003 | Jensen et al. | |
| 2003/0157117 | A1 | 8/2003 | Rasmussen et al. | |
| 2004/0043935 | A1 | 3/2004 | Frangione et al. | |
| 2005/0123553 | A1 | 6/2005 | Monsonego et al. | |
| 2006/0135403 | A1 | 6/2006 | Gervais et al. | |
| 2006/0142506 | A1 | 6/2006 | Breitenkamp et al. | |
| 2006/0172914 | A1 | 8/2006 | Breitenkamp et al. | |
| 2006/0240092 | A1 | 10/2006 | Breitenkamp et al. | |
| 2007/0010435 | A1 | 1/2007 | Frangione et al. | |
| 2007/0041945 | A1 | 2/2007 | Jensen et al. | |
| 2007/0098721 | A1 | 5/2007 | Hillen et al. | |
| 2007/0197452 | A1 | 8/2007 | Mclaurin | |
| 2007/0218491 | A1 | 9/2007 | Vasan et al. | |
| 2008/0207913 | A1 | 8/2008 | Breitenkamp et al. | |
| 2009/0092554 | A1 | 4/2009 | Skaff et al. | |
| 2010/0136063 | A1 | 6/2010 | Cao et al. | |

FOREIGN PATENT DOCUMENTS

| | | | |
|---|---|---|---|
| WO | WO 99/41279 | A3 | 8/1999 |
| WO | WO 01/62284 | A2 | 8/2001 |
| WO | WO 02/096937 | A3 | 12/2002 |
| WO | WO 03/015812 | A2 | 2/2003 |
| WO | WO 2004/018997 | A2 | 3/2004 |
| WO | WO 2004/024090 | A2 | 3/2004 |
| WO | WO 2006/107903 | A2 | 10/2006 |
| WO | WO 2007/064917 | A2 | 6/2007 |
| WO | WO 2008/098371 | A1 | 8/2008 |
| WO | WO 2008/106657 | A2 | 9/2008 |

OTHER PUBLICATIONS

Abbas, N. et al. "Up-regulation of the inflammatory cytokines IFN-γ and IL-12 and down-regulation of IL-4 in cerebral cortex regions of $APP_{SWE}$ transgenic mice" *Journal of Neuroimmunology*, 2002, 126:50-57.

Allen, C. at al. "Nano-engineering block copolymer aggregates for drug delivery" *Colloids and Surfaces B: Biointerfaces*, 1999, 16:3-27.

Bard, F. et al. "Peripherally administered antibodies against amyloid β-peptide enter the central nervous system and reduce pathology in a mouse model of Alzheimer disease" *Nature Medicine*, Aug. 2000, 6(8):916-919.

Bayer, A.J. et al. "Evaluation of the safety and immunogenicity of synthetic Aβ42 (AN1792) in patients with AD" *Neurology*, 2005, 64:94-101.

Cannan, R.K. et al. "Complex Formation between Carboxylic Acids and Divalent Metal Cations" *Journal of the American Chemical Society*, Oct. 1938, 60(10):2314-2320.

Chauhan, N.B. "Intracerebroventricular Passive Immunization With Anti-OligoAβ Antibody in TgCRND8" *Journal of Neuroscience Research*, 2007, 85:451-463.

Deiters, A. et al. "Adding Amino Acids with Novel Reactivity to the Genetic Code of *Saccharomyces cerevisiae*" *J. Am. Chem. Soc.*, 2003, 125:11782-11783.

(Continued)

*Primary Examiner* — Daniel E Kolker

(74) *Attorney, Agent, or Firm* — Saliwanchik, Lloyd & Eisenschenk

(57) ABSTRACT

The application describes several mutant amyloid beta peptides and specific regions which are useful in the therapeutic and diagnostic of neurological diseases. The application further describes methods of using these mutant peptides as treatment and reagents for diagnosis of diseases. The application further describes diagnostic kits and pharmaceutical compositions for use in therapy to treat neurological diseases including but not limited to Alzheimer's disease and various forms of mild cognitive impairments.

22 Claims, 12 Drawing Sheets

OTHER PUBLICATIONS

Dickey, C.A. et al. "Selectively Reduced Expression of Synaptic Plasticity-Related Genes in Amyloid Precursor Protein + Presenilin-1 Transgenic Mice" *The Journal of Neuroscience*, Jun. 2003, 23(12):5219-5226.
Eby, G.A. "Zinc ion availability—the determinant of efficacy in zinc lozenge treatment of common colds" *Journal of Antimicrobial Chemotherapy*, 1997, 40:483-493.
Kirkitadze, M.D. et al. "Paradigm Shifts in Alzheimer's Disease and Other Neurodegenerative Disorders: The Emerging Role of Oligomeric Assemblies" *Journal of Neuroscience Research*, 2002, 69:567-577.
Kolb, H.C. et al. "Click Chemistry: Diverse Chemical Function from a Few Good Reactions" *Angew. Chem. Int.*, 2001, 40:2004-2021.
Link, A.J. et al. "Presentation and Detection of Azide Functionality in Bacterial Cell Surface Proteins" *J. Am. Chem. Soc.* 2004, 126(34):10598-10602.
Mathews, P.M. et al. "Setback for an Alzheimer's disease vaccine Lessons learned" *Neurology*, 2003, 61:7-8.
Monsonego, A. et al. "Increased T cell reactivity to amyloid β protein in older humans and patients with Alzheimer disease" *J. Clin. Invest.*, Aug. 2003, 112(3):415-422.
Morgan, D. "Antibody therapy for Alzheimer's disease" *Expert Rev. Vaccines*, 2003, 2(1):89-95.
Morgan, D. et al. "Aβ peptide vaccination prevents memory loss in an animal model of Alzheimer's disease" *Nature*, Dec. 2000, 408:982-985.
Nilsson, L.N.G. et al. "Cognitive impairment in PDAPP mice depends on ApoE and ACT-catalyzed amyloid formation" *Neurobiology of Aging*, 2004, 25:1153-1167.
Parihar, M.S. et al. "Alzheimer's disease pathogenesis and therapeutic interventions" *Journal of Clinical Neuroscience*, 2004, 11(5):456-467.
Walsh, D.M. et al. "Deciphering the Molecular Basis of Memory Failure in Alzheimer's Disease" *Neuron*, Sep. 2004, 44:181-193.
Wang, Q. et al. "Bioconjugation by Copper(I)-Catalyzed Azide-Alkyne [3+2] Cycloaddition" *J. Am. Chem. Soc.*, 2003, 125:3192-3193.
Zuliani, G. et al. "Plasma cytokines profile in older subjects with late onset Alzheimer's disease or vascular dementia" *Journal of Psychiatric Research*, 2007, 41:686-693.
Cao, C. et al. "Development of Plasmid DNA Vaccines Against Beta Amyloid Protein for Prophylactic and/or Therapeutic Use Against Transgenic Mouse Model of Amyloid Deposition" *Society for Neuroscience Abstracts*, 2001, 27:1717.
Cao, C. et al. "Successful adjuvant-free vaccination of BALB/c mice with mutated amyloid β peptides" *BMC Neuroscience*, Feb. 2008, 9(25):1-11.
Ghochikyan, A. et al. "Aβ-Immunotherapy for Alzheimer's Disease Using Mannan-Amyloid-Beta Peptide Immunoconjugates" *DNA and Cell Biology*, Oct. 2006, 25(10):571-580.
Kutzler, M.A. et al. "Mapping of immune responses following wild-type and mutant ABeta42 plasmid or peptide vaccination in different mouse haplotypes and HLA class II transgenic mice" *Vaccine*, 2006, 24(21):4630-4639.
Li, Q. et al. "Dutch Mutation Aβ Amyloid Peptide Enhanced Immune Response in APP Transgenic Mice" *Society for Neuroscience Abstract Viewer and Itinerary Planner*, 2003, Program No. 526.12, p. 1.

* cited by examiner

SEQUENCE LISTING

<160> NUMBER OF SEQ ID NOS: 30

<210> SEQ ID NO 1
<211> LENGTH: 42
<212> TYPE: PRT
<213> ORGANISM: Artificial Sequence
<220> FEATURE:
<223> OTHER INFORMATION: Amyloid beta mutant P22W

<400> SEQUENCE: 1

Asp Ala Glu Phe Arg His Asp Ser Gly Tyr Glu Val His His Gln Lys
1 5 10 15

Leu Val Phe Phe Ala Trp Asp Val Gly Ser Asn Lys Gly Ala Ile Ile
20 25 30

Gly Leu Met Val Gly Gly Val Val Ile Ala
35 40

<210> SEQ ID NO 2
<211> LENGTH: 42
<212> TYPE: PRT
<213> ORGANISM: Artificial Sequence
<220> FEATURE:
<223> OTHER INFORMATION: Amyloid beta mutant P24M

<400> SEQUENCE: 2

Asp Ala Glu Phe Arg His Asp Ser Gly Tyr Glu Val His His Gln Lys
1 5 10 15

Leu Val Phe Phe Ala Glu Asp Met Gly Ser Asn Lys Gly Ala Ile Ile
20 25 30

Gly Leu Met Val Gly Gly Val Val Ile Ala
35 40

<210> SEQ ID NO 3
<211> LENGTH: 42
<212> TYPE: PRT
<213> ORGANISM: Artificial Sequence
<220> FEATURE:
<223> OTHER INFORMATION: Amyloid beta mutant P24G

<400> SEQUENCE: 3

Asp Ala Glu Phe Arg His Asp Ser Gly Tyr Glu Val His His Gln Lys
1 5 10 15

Leu Val Phe Phe Ala Glu Asp Gly Gly Ser Asn Lys Gly Ala Ile Ile
20 25 30

Gly Leu Met Val Gly Gly Val Val Ile Ala
35 40

<210> SEQ ID NO 4
<211> LENGTH: 42
<212> TYPE: PRT

<213> ORGANISM: Artificial Sequence
<220> FEATURE:
<223> OTHER INFORMATION: Amyloid beta mutant P22F

<400> SEQUENCE: 4

Asp Ala Glu Phe Arg His Asp Ser Gly Tyr Glu Val His His Gln Lys
1 5 10 15

Leu Val Phe Phe Ala Phe Asp Val Gly Ser Asn Lys Gly Ala Ile Ile
20 25 30

Gly Leu Met Val Gly Gly Val Val Ile Ala
35 40

<210> SEQ ID NO 5
<211> LENGTH: 42
<212> TYPE: PRT
<213> ORGANISM: Artificial Sequence
<220> FEATURE:
<223> OTHER INFORMATION: Amyloid beta mutant P22R

<400> SEQUENCE: 5

Asp Ala Glu Phe Arg His Asp Ser Gly Tyr Glu Val His His Gln Lys
1 5 10 15

Leu Val Phe Phe Ala Arg Asp Val Gly Ser Asn Lys Gly Ala Ile Ile
20 25 30

Gly Leu Met Val Gly Gly Val Val Ile Ala
35 40

<210> SEQ ID NO 6
<211> LENGTH: 9
<212> TYPE: PRT
<213> ORGANISM: Artificial Sequence
<220> FEATURE:
<223> OTHER INFORMATION: Wild type (PWT) mutation

<400> SEQUENCE: 6

Lys Leu Val Phe Phe Ala Glu Asp Val
1 5

<210> SEQ ID NO 7
<211> LENGTH: 9
<212> TYPE: PRT
<213> ORGANISM: Artificial Sequence
<220> FEATURE:
<223> OTHER INFORMATION: Flemish mutation (PFM)

<400> SEQUENCE: 7

Lys Leu Val Phe Phe Gly Glu Asp Val
1 5

<210> SEQ ID NO 8
<211> LENGTH: 9
<212> TYPE: PRT
<213> ORGANISM: Artificial Sequence
<220> FEATURE:
<223> OTHER INFORMATION: Dutch mutation (PDM)

<400> SEQUENCE: 8

Lys Leu Val Phe Phe Ala Gln Asp Val
1 5

<210> SEQ ID NO 9
<211> LENGTH: 9
<212> TYPE: PRT
<213> ORGANISM: Artificial Sequence
<220> FEATURE:
<223> OTHER INFORMATION: Flemish plus Dutch (PFDM) mutation -continued

<400> SEQUENCE: 9

```
Lys Leu Val Phe Phe Gly Gln Asp Val
1               5
```

<210> SEQ ID NO 10
<211> LENGTH: 9
<212> TYPE: PRT
<213> ORGANISM: Artificial Sequence
<220> FEATURE:
<223> OTHER INFORMATION: New mutation1 (P22W)

<400> SEQUENCE: 10

```
Lys Leu Val Phe Phe Ala Trp Asp Val
1               5
```

<210> SEQ ID NO 11
<211> LENGTH: 9
<212> TYPE: PRT
<213> ORGANISM: Artificial Sequence
<220> FEATURE:
<223> OTHER INFORMATION: New mutation2 (P24G)

<400> SEQUENCE: 11

```
Lys Leu Val Phe Phe Ala Glu Asp Gly
1               5
```

<210> SEQ ID NO 12
<211> LENGTH: 42
<212> TYPE: PRT
<213> ORGANISM: Artificial Sequence
<220> FEATURE:
<223> OTHER INFORMATION: Abeta peptide 1-42 (mouse, rat, Chinese hamster)

<400> SEQUENCE: 12

```
Asp Ala Glu Phe Gly His Asp Ser Gly Phe Glu Val Arg His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```

<210> SEQ ID NO 13
<211> LENGTH: 42
<212> TYPE: PRT
<213> ORGANISM: Artificial Sequence
<220> FEATURE:
<223> OTHER INFORMATION: Abeta peptide 1-42 (frog)

<400> SEQUENCE: 13

```
Asp Ser Glu Tyr Arg His Asp Thr Ala Tyr Glu Val His His Gln Lys
1               5                   10                  15

Leu Val Phe Phe Ala Glu Glu Val Gly Ser Asn Lys Gly Ala Ile Ile
            20                  25                  30

Gly Leu Met Val Gly Gly Val Val Ile Ala
        35                  40
```

<210> SEQ ID NO 14
<211> LENGTH: 42
<212> TYPE: PRT
<213> ORGANISM: Artificial Sequence
<220> FEATURE:
<223> OTHER INFORMATION: Abeta peptide 1-42 (fish)

<400> SEQUENCE: 14

Glu Thr Glu Phe Gln Gln Asp Ser Gly Tyr Glu Val His His Gln Lys
1 5 10 15

Leu Val Phe Phe Pro Lys Asp Val Gly Ser Asn Lys Gly Ala Ile Ile
20 25 30

Gly Leu Met Val Gly Gly Val Val Ile Ala
35 40

<210> SEQ ID NO 15
<211> LENGTH: 42
<212> TYPE: PRT
<213> ORGANISM: Artificial Sequence
<220> FEATURE:
<223> OTHER INFORMATION: Abeta peptide 1-42 (zebra fish)

<400> SEQUENCE: 15

Leu Arg Met Glu Ala Glu Glu Arg His Ser Glu Val Tyr His Gln Lys
1 5 10 15

Leu Val Phe Phe Ala Glu Asp Val Ser Ser Asn Lys Gly Ala Ile Ile
20 25 30

Gly Leu Met Val Gly Gly Val Val Ile Ala
35 40

<210> SEQ ID NO 16
<211> LENGTH: 34
<212> TYPE: PRT
<213> ORGANISM: Artificial Sequence
<220> FEATURE:
<223> OTHER INFORMATION: PDM34

<400> SEQUENCE: 16

Asp Ala Glu Phe Arg His Asp Ser Gly Tyr Glu Val His His Gln Lys
1 5 10 15

Leu Val Phe Phe Ala Gln Asp Val Gly Ser Asn Lys Gly Ala Ile Ile
20 25 30

Gly Leu

<210> SEQ ID NO 17
<211> LENGTH: 33
<212> TYPE: PRT
<213> ORGANISM: Artificial Sequence
<220> FEATURE:
<223> OTHER INFORMATION: PDM33

<400> SEQUENCE: 17

Asp Ala Glu Phe Arg His Asp Ser Gly Tyr Glu Val His His Gln Lys
1 5 10 15

Leu Val Phe Phe Ala Gln Asp Val Gly Ser Asn Lys Gly Ala Ile Ile
20 25 30

Gly

<210> SEQ ID NO 18
<211> LENGTH: 32
<212> TYPE: PRT
<213> ORGANISM: Artificial Sequence
<220> FEATURE:
<223> OTHER INFORMATION: PDM32

<400> SEQUENCE: 18

Asp Ala Glu Phe Arg His Asp Ser Gly Tyr Glu Val His His Gln Lys
1 5 10 15

Leu Val Phe Phe Ala Gln Asp Val Gly Ser Asn Lys Gly Ala Ile Ile
20 25 30

-continued

```
<210> SEQ ID NO 19
<211> LENGTH: 31
<212> TYPE: PRT
<213> ORGANISM: Artificial Sequence
<220> FEATURE:
<223> OTHER INFORMATION: PDM31

<400> SEQUENCE: 19

Asp Ala Glu Phe Arg His Asp Ser Gly Tyr Glu Val His His Gln Lys
1               5                   10                  15

Leu Val Phe Phe Ala Gln Asp Val Gly Ser Asn Lys Gly Ala Ile
            20                  25                  30


<210> SEQ ID NO 20
<211> LENGTH: 30
<212> TYPE: PRT
<213> ORGANISM: Artificial Sequence
<220> FEATURE:
<223> OTHER INFORMATION: PDM30

<400> SEQUENCE: 20

Asp Ala Glu Phe Arg His Asp Ser Gly Tyr Glu Val His His Gln Lys
1               5                   10                  15

Leu Val Phe Phe Ala Gln Asp Val Gly Ser Asn Lys Gly Ala
            20                  25                  30


<210> SEQ ID NO 21
<211> LENGTH: 29
<212> TYPE: PRT
<213> ORGANISM: Artificial Sequence
<220> FEATURE:
<223> OTHER INFORMATION: PDM29

<400> SEQUENCE: 21

Asp Ala Glu Phe Arg His Asp Ser Gly Tyr Glu Val His His Gln Lys
1               5                   10                  15

Leu Val Phe Phe Ala Gln Asp Val Gly Ser Asn Lys Gly
            20                  25


<210> SEQ ID NO 22
<211> LENGTH: 28
<212> TYPE: PRT
<213> ORGANISM: Artificial Sequence
<220> FEATURE:
<223> OTHER INFORMATION: PDM28

<400> SEQUENCE: 22

Asp Ala Glu Phe Arg His Asp Ser Gly Tyr Glu Val His His Gln Lys
1               5                   10                  15

Leu Val Phe Phe Ala Gln Asp Val Gly Ser Asn Lys
            20                  25


<210> SEQ ID NO 23
<211> LENGTH: 27
<212> TYPE: PRT
<213> ORGANISM: Artificial Sequence
<220> FEATURE:
<223> OTHER INFORMATION: PDM27

<400> SEQUENCE: 23

Asp Ala Glu Phe Arg His Asp Ser Gly Tyr Glu Val His His Gln Lys
1               5                   10                  15

Leu Val Phe Phe Ala Gln Asp Val Gly Ser Asn
            20                  25
```

<210> SEQ ID NO 24
<211> LENGTH: 26
<212> TYPE: PRT
<213> ORGANISM: Artificial Sequence
<220> FEATURE:
<223> OTHER INFORMATION: PDM26

<400> SEQUENCE: 24

```
Asp Ala Glu Phe Arg His Asp Ser Gly Tyr Glu Val His His Gln Lys
1               5                   10                  15

Leu Val Phe Phe Ala Gln Asp Val Gly Ser
            20                  25
```

<210> SEQ ID NO 25
<211> LENGTH: 35
<212> TYPE: PRT
<213> ORGANISM: Artificial Sequence
<220> FEATURE:
<223> OTHER INFORMATION: Abeta 1-35 (PWT35)

<400> SEQUENCE: 25

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met
        35
```

<210> SEQ ID NO 26
<211> LENGTH: 35
<212> TYPE: PRT
<213> ORGANISM: Artificial Sequence
<220> FEATURE:
<223> OTHER INFORMATION: Abeta 1-35 (PFM35) with Flemish mutation

<400> SEQUENCE: 26

```
Asp Ala Glu Phe Arg His Asp Ser Gly Tyr Glu Val His His Gln Lys
1               5                   10                  15

Leu Val Phe Phe Gly Glu Asp Val Gly Ser Asn Lys Gly Ala Ile Ile
            20                  25                  30

Gly Leu Met
        35
```

<210> SEQ ID NO 27
<211> LENGTH: 35
<212> TYPE: PRT
<213> ORGANISM: Artificial Sequence
<220> FEATURE:
<223> OTHER INFORMATION: Abeta 1-35 (PDM35) with Dutch mutation

<400> SEQUENCE: 27

```
Asp Ala Glu Phe Arg His Asp Ser Gly Tyr Glu Val His His Gln Lys
1               5                   10                  15

Leu Val Phe Phe Ala Gln Asp Val Gly Ser Asn Lys Gly Ala Ile Ile
            20                  25                  30

Gly Leu Met
        35
```

<210> SEQ ID NO 28
<211> LENGTH: 35
<212> TYPE: PRT
<213> ORGANISM: Artificial Sequence
<220> FEATURE:

-continued

```
<223> OTHER INFORMATION: Abeta 1-35 (PFDM35) with Flemish and Dutch
      mutation

<400> SEQUENCE: 28

Asp Ala Glu Phe Arg His Asp Ser Gly Tyr Glu Val His His Gln Lys
1               5                   10                  15

Leu Val Phe Phe Gly Gln Asp Val Gly Ser Asn Lys Gly Ala Ile Ile
            20                  25                  30

Gly Leu Met
        35


<210> SEQ ID NO 29
<211> LENGTH: 35
<212> TYPE: PRT
<213> ORGANISM: Artificial Sequence
<220> FEATURE:
<223> OTHER INFORMATION: Abeta 1-35 (PM35) (new mutation)

<400> SEQUENCE: 29

Asp Ala Glu Phe Arg His Asp Ser Gly Tyr Glu Val His His Gln Lys
1               5                   10                  15

Leu Val Phe Phe Ala Glu Ala Val Gly Ser Asn Lys Gly Ala Ile Ile
            20                  25                  30

Gly Leu Met
        35


<210> SEQ ID NO 30
<211> LENGTH: 35
<212> TYPE: PRT
<213> ORGANISM: Artificial Sequence
<220> FEATURE:
<223> OTHER INFORMATION: Abeta 1-35 (P22W) (new mutation)

<400> SEQUENCE: 30

Asp Ala Glu Phe Arg His Asp Ser Gly Tyr Glu Val His His Gln Lys
1               5                   10                  15

Leu Val Phe Phe Ala Glu Ile Val Gly Ser Asn Lys Gly Ala Ile Ile
            20                  25                  30

Gly Leu Met
        35
```

AMYLOID BETA PEPTIDES AND METHODS OF USE

CROSS-REFERENCE TO RELATED APPLICATIONS

This application is the National. Stage of International Application Number PCT/US2007/081235, filed Oct. 12, 2007, which claims the benefit of U.S. Provisional Application Ser. No. 60/851,966, filed Oct. 16, 2006 and U.S. Provisional Application Ser. No. 60/898,080, filed Jan. 29, 2007, each of which is hereby incorporated by reference herein in its entirety, including any figures, tables, nucleic acid sequences, amino acid sequences, and drawings.

BACKGROUND

Pathological, biochemical and genetic studies have implicated the Abeta peptide in the pathogenesis of Alzheimer's disease and suggested that reducing Abeta in the brain should be therapeutic.

One method for reducing Abeta in the brain is vaccination, first demonstrated by Shenk and colleagues who used Aβ 1-42 as an active vaccine and succeeded in reducing amyloid load in a mouse model of AD. It was then shown that the use of beta amyloid 1-42 as an active vaccine not only induced an effective remission of beta amyloid plaques in the brain but also led to cognitive and behavioral improvements. Additionally, passive immunotherapy was also shown to lead to similar results as the active beta-amyloid vaccine study.

Although vaccination was clearly effective in the mouse models of AD, the increased presence of antigen-presenting, HLA-DR-positive and other immunoregulatory cells together with increased levels of inflammatory cytokines and acute phase reactants in the vicinity of the neuropathology indicated that the vaccination triggered an inflammatory immune response The few mutations in the APP gene that result in mutant Aβ peptides cause special forms of autosomal dominant AD. For example, the Dutch and Flemish mutations are known to cause patterns of aggregation that strongly differ from those with wild type Aβ peptide and result in different clinical manifestations of the disease. The increased success with vaccinations using amyloid β peptide in mouse models of AD encouraged a human clinical trial. The trial was a randomized, multi-centered, placebo-controlled, double-blind trial using wild type amyloid beta 1-42 peptide, termed AN1792, as a vaccine in combination with the adjuvant QS-21 and polysorbate 80 as stabilizer. The trial included patients aged 50 to 85 years with probable AD, as determined by the Mini-Mental State Examination (MMSE). Phase II of the trial was suspended due to an occurrence of meningoencephalitis in a small (6%) subset of patients. However, in a follow up study of the vaccinated patients, some clinical benefits of the vaccination including reduced AD-like pathology and improved cognition in the patients could be demonstrated. In addition, there were indications that the inflammatory response might actually have been triggered by the adjuvant or the stabilizer and not the antigen. Further analysis is required to determine the mechanism of the vaccine-induced neuroinflammation and the associated meningoencephalitis.

It has been theorized that the Alzheimer's disease related inflammation could be a form of autoimmunity that potentially marks a more specific and progressive state of the disease. Preliminary data, such as the measurement of pro-inflammatory cytokines after vaccination with and without adjuvant, suggests that the causes of many of the brain tissue inflammation side effects of the vaccines are possibly due to the adjuvants that carry the antigen. In fact, other studies have shown that adjuvants induce significant pro-inflammatory cytokine expression in vivo including up-regulation of TNF-α, IFNγ, and IL-4 even without being co-delivered with an antigen.

Another problem associated with the adverse effects of vaccination is related to the T cell epitope that resides in the Aβ 1-42 peptides. Thus, numerous approaches have been proposed for vaccine development. A derivative Abeta peptide without a T cell epitope has been applied with different methods. In addition, viral delivery, Abeta combined with bacterial toxins, and DNA vaccines are all applied with the goal to develop a safe vaccine.

There are mounting evidences indicates that the Aβ 1-42 peptide and Aβ 1-40 peptide, generated from Amyloid precursor protein (APP), are the major etiological factors for AD. These peptides are the main constituents of the amyloid deposits found in AD patient's brains. Aβ 1-42 was used as an active vaccine to effectively remove beta amyloid plaques in the brain. Corresponding behavioral improvements were also observed. Passive immunotherapy by using antibodies against Aβ 1-42 peptide/protein can effectively inhibit the deposition of Aβ in the brain and this has significantly decreased memory deficits in an APP/PS1 transgenic mouse model.

The effectiveness of the peptide therapy approach in clearance of plaque in the mouse model and in patients is not in question. The hope for AD vaccine is to find a solution to the adverse effects caused by vaccine in humans. However, the pathological role of Beta amyloid in AD obviously remains strong and beta amyloid is currently the gold standard for evaluating treatment. Regardless of which method is used to treat AD, the most prominent factor is still beta amyloid peptide levels in vivo, so a safer and effective vaccine remains a very promising and cost-effective approach to either curing AD patients or at least ameliorating AD development.

FIELD OF THE INVENTION

This invention relates to the field of mammalian neuronal cell disorders, and in particular, to methods for suppressing inflammatory mediators related to neuronal disorders, identifying effective compounds with biological active equivalents, and therapies and compositions using such compounds, useful for the prevention and treatment of diseases associated with progressive loss of intellectual capacities in humans.

The neurological disorder that is most widely known for its progressive loss of intellectual capacities is Alzheimer's disease (AD). Worldwide, about 20 million people suffer from Alzheimer's disease. AD is clinically characterized by the initial loss of memory, followed by disorientation, impairment of judgment and reasoning, which is commonly referred to as cognitive impairment, and ultimately by full dementia. AD patients finally lapse into a severely debilitated, immobile state between four and twelve years after onset of the disease.

The key pathological evidence for AD is the presence of extracellular amyloid plaques and intracellular tau tangles in the brain, which are associated with neuronal degeneration. The extracellular amyloid plaques are believed to result from an increase in the insoluble amyloid beta peptide 1-42 produced by the metabolism of amyloid-beta precursor protein (APP). Following β, γ secretion, these amyloid beta 1-42 peptides form amyloid fibrils more readily than the amyloid beta 1-40 peptides, which are predominantly produced in healthy people. It appears that the amyloid beta peptide is on top of the neurotoxic cascade: experiments show that amyloid beta fibrils, when injected into the brains of P301 L tau transgenic mice, enhance the formation of neurofibrillary tangles. In fact, a variety of amyloid beta peptides have been identified as amyloid beta peptides 1-42, 1-40, 1-39, 1-38, 1-37, which can be found in plaques and are often seen in cerebral spinal fluid.

The amyloid beta peptides are generated (or processed) from the membrane anchored APP, after cleavage by beta secretase and gamma secretase at position 671 and 711 or 713, respectively. In addition, high activity of beta secretase results in a shift of the cleavage at position 1 to position 11. Cleavage of amyloid-beta precursor protein by alpha secretase activity will generate Aβ 1-17 and gamma secretase activity at 40 or 42 generates the non-pathological p3 peptide. Beta secretase was identified as the membrane anchored aspartyl protease BACE, while gamma secretase is a protein complex comprising presenilin 1 (PS1) or presenilin 2 (PS2), nicastrin, Anterior Pharynx Defective 1 (APH1) and Presenilin Enhancer 2 (PEN2). Of these proteins, the presenilins are widely thought to constitute the catalytic activity of the gamma secretase, while the other components play a role in the maturation and localization of the complex. The identity of the alpha secretase is still illustrious, although some results point towards the proteases ADAM 10 and TACE, which could have redundant functions.

A small fraction of AD cases (mostly early onset AD) are caused by autosomal dominant mutations in the genes encoding presenilin 1 and 2 (PS1; PS2) and the amyloid-beta precursor protein (APP), and it has been shown that mutations in APP, PS1 and PS2 alter the metabolism of amyloid-beta precursor protein leading to such increased levels of amyloid beta 1-42 produced in the brain. Although no mutations in PS1, PS2 and amyloid-beta precursor protein have been identified in late onset AD patients, the pathological characteristics are highly similar to the early onset AD patients. These increased levels of amyloid beta peptide could originate progressively with age from disturbed amyloid-beta precursor protein processing (e.g. high cholesterol levels enhance amyloid beta peptide production) or from decreased amyloid beta peptide catabolism. Therefore, it is generally accepted that AD in late onset AD patients is also caused by aberrant increased amyloid peptide levels in the brains. The level of these amyloid beta peptides, and more particularly amyloid-beta peptide 1-42, is increased in Alzheimer patients compared to the levels of these peptides in healthy persons.

The work described herein will enable one of ordinary skill in the art to devise a kits for therapeutic vaccines and pharmaceuticals or diagnostics and allow earlier detection of Alzheimer's symptoms through detection of amyloid beta mutation sequences.

SUMMARY OF THE INVENTION

The present invention relates to novel peptides having the amino acid sequences selected from the group DAEFRHDSGYEVHHQKLVFFAWDVGSNKGAIIGLMVGGVVIA (Amyloid beta mutant P22W) (SEQ ID NO:1), DAEFRHDSGYEVHHQKLVFFAEDMGSNKGAIIGLMVGGVVIA (Amyloid beta mutant P24M) (SEQ ID NO:2), DAEFRHDSGYEVHHQKLVFFAEDGGSNKGAIIGLMVGGVVIA (Amyloid beta mutant P24G) (SEQ ID NO:3), DAEFRHDSGYEVHHQKLVFFAFDVGSNKGAIIGLMVGGVVIA (Amyloid beta mutant P22F) (SEQ ID NO:4), and DAEFRIIDSGYEVHHQKLVFFARDVGSNKGAIIGLMVGGVVIA (Amyloid beta mutant P22R) (SEQ ID NO:5), and mutant fragments or biological equivalents thereof.

One aspect of the present invention is a method for identifying a compound that suppresses the production of inflammatory proteins such as cytokines and chemokines from cells or in an animal treated with the peptide of the invention having the amino acid sequence DAEFRHDSGYEVHHQKLVFFAWDVGSNKGAIIGLMVGGVVIA (Amyloid beta mutant P22W) (SEQ ID NO:1), DAEFRHDSGYEVHHQKLVFFAEDMGSNKGAIIGLMVGGVVIA (Amyloid beta mutant P24M) (SEQ ID NO:2), DAEFRHDSGYEVHHQKLVFFAEDGGSNKGAIIGLMVGGVVIA (Amyloid beta mutant P24G) (SEQ ID NO:3), DAEFRHDSGYEVHHQKLVFFAFDVGSNKGAIIGLMVGGVVIA (Amyloid beta mutant P22F) (SEQ ID NO:4), or DAEFRHDSGYEVHHQKLVFFARDVGSNKGAIIGLMVGGVVIA (Amyloid beta mutant P22R) (SEQ ID NO:5), or mutant fragments or biological equivalents thereof.

Another aspect of the invention relates to a kit comprising the peptide of the present invention having the amino acid sequence DAEFRHDSGYEVHHQKLVFFAWDVGSNKGAIIGLMVGGVVIA (Amyloid beta mutant P22W) (SEQ ID NO:1), DAEFRHDSGYEVHHQKLVFFAEDMGSNKGAIIGLMVGGVVIA (Amyloid beta mutant P24M) (SEQ ID NO:2), DAEFRHDSGYEVHHQKLVFFAEDGGSNKGAIIGLMVGGVVIA (Amyloid beta mutant P24G) (SEQ ID NO:3), DAEFRHDSGYEVHHQKLVFFAFDVGSNKGAIIGLMVGGVVIA (Amyloid beta mutant P22F) (SEQ ID NO:4), or DAEFRHDSGYEVHHQKLVFFARDVGSNKGAIIGLMVGGVVIA (Amyloid beta mutant P22R) (SEQ ID NO:5), or mutant fragments or biological equivalents thereof.

Another aspect of the invention relates to a pharmaceutical composition of the present invention having the amino acid sequence DAEFRHDSGYEVHHQKLVFFAWDVGSNKGAIIGLMVGGVVIA (Amyloid beta mutant P22W) (SEQ ID NO:1), DAEFRHDSGYEVHHQKLVFFAEDMGSNKGAIIGLMVGGVVIA (Amyloid beta mutant P24M) (SEQ ID NO:2), DAEFRHDSGYEVHHQKLVFFAEDGGSNKGAIIGLMVGGVVIA (Amyloid beta mutant P24G) (SEQ ID NO:3), DAEFRHDSGYEVHHQKLVFFAFDVGSNKGAIIGLMVGGVVIA (Amyloid beta mutant P22F) (SEQ ID NO:4), or DAEFRHDSGYEVHHQKLVFFARDVGSNKGAIIGLMVGGVVIA (Amyloid beta mutant P22R) (SEQ ID NO:5), mutant fragments or biological equivalents thereof and an acceptable carrier.

Another aspect of the invention relates to a peptide having the amino acid sequence DAEFRHDSGYEVHHQKLVFFAWDVGSNKGAIIGLMVGGVVIA (Amyloid beta mutant P22W) (SEQ ID NO:1), DAEFRHDSGYEVHHQKLVFFAEDMGSNKGAIIGLMVGGVVIA (Amyloid beta mutant P24M) (SEQ ID NO:2), DAEFRHDSGYEVHHQKLVFFAEDGGSNKGAIIGLMVGGVVIA (Amyloid beta mutant P24G) (SEQ ID NO:3), DAEFRHDSGYEVHHQKLVFFAFDVGSNKGAIIGLMVGGVVIA (Amyloid beta mutant P22F) (SEQ ID NO:4), or DAEFRHDSGYEVHHQKLVFFARDVGSNKGAIIGLMVGGVVIA (Amyloid beta mutant P22R) (SEQ ID NO:5), mutant fragments or biological equivalents thereof.

Another aspect of the invention is a method of treatment or prevention of a condition involving cognitive impairment, or a susceptibility to the condition, in a subject suffering or susceptible thereto, by administering a pharmaceutical composition comprising an effective amount of the peptide having the amino acid sequence DAEFRHDSGYEVHHQKLVFFAWDVGSNKGAIIGLMVGGVVIA (Amyloid beta mutant P22W) (SEQ ID NO:1), DAEFRHDSGYEVHHQKLVFFAEDMGSNKGAIIGLMVGGVVIA (Amyloid beta mutant P24M) (SEQ ID NO:2), DAEFRHDSGYEVHHQKLVF- FAEDGGSNKGAIIGLMVGGVVIA (Amyloid beta mutant P24G) (SEQ ID NO:3), DAEFRHDSGYEVHHQKLVF-FAFDVGSNKGAIIGLMVGGVVIA (Amyloid beta mutant P22F) (SEQ ID NO:4), or DAEFRHDSGYEVHHQKLVF-FARDVGSNKGAIIGLMVGGVVIA (Amyloid beta mutant P22R) (SEQ ID NO:5), mutant fragments or biological equivalents thereof.

BRIEF DESCRIPTION OF THE DRAWINGS

FIG. 1A Illustrates that adjuvant free vaccination with all peptide can induce high antibody response after three inoculations. FIG. 1B. Demonstrates antisera cross reaction to coating peptide.

DETAILED DESCRIPTION OF THE INVENTION

Figure 1:
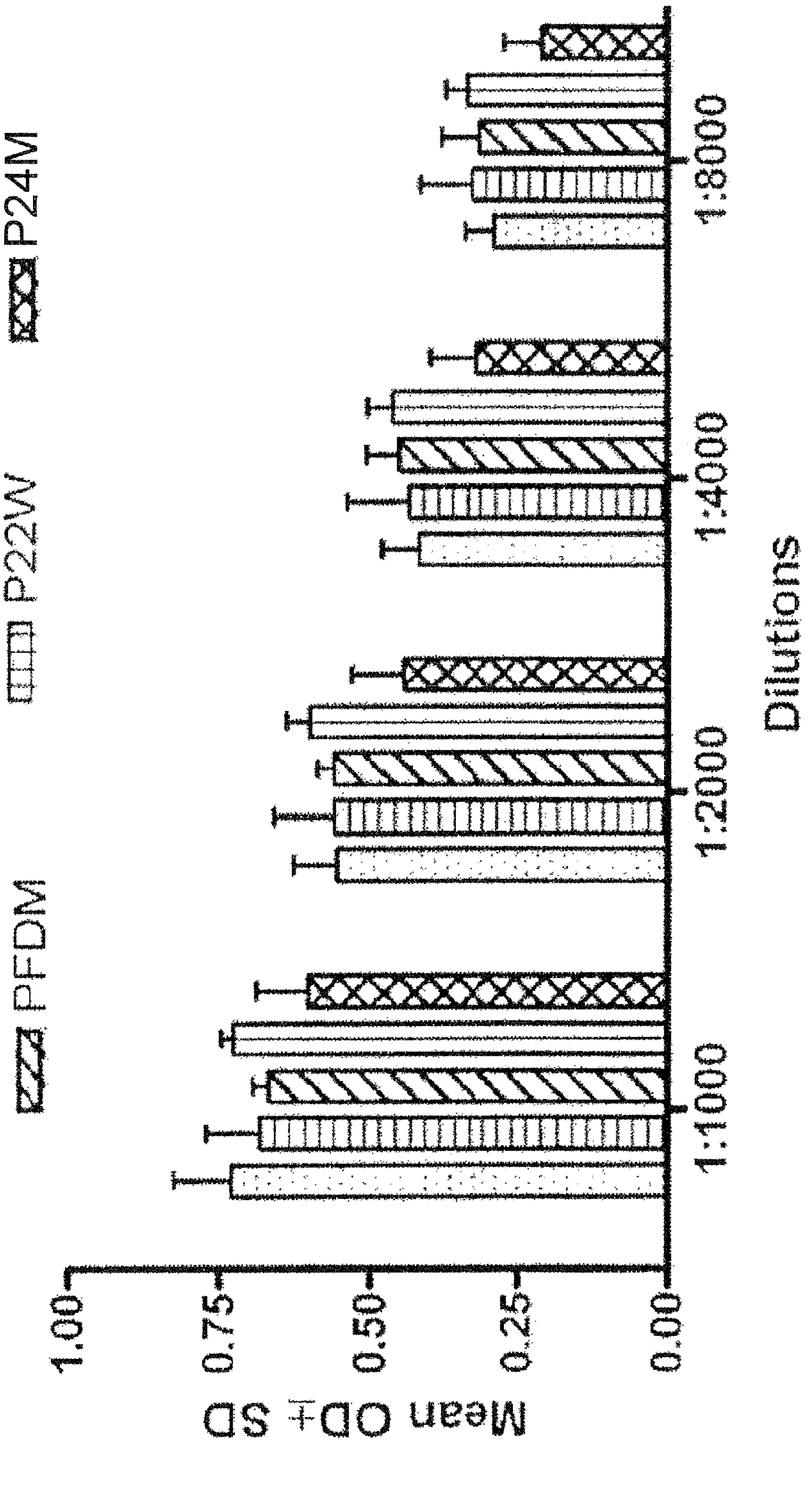
FIG. 1: Demonstrates the antibody responses in mice injected peptide stimulated DCs after two inoculations. Endpoint antibody titer is greater than 1:8000 and there are no differences among all those peptides that can induce antibody response. There is no antibody produce in the group received DCs treated by wild-type peptide.

The following terms are intended to have the meanings presented therewith below and are useful in understanding the description of the present invention is not meant to limit the scope of the invention.

DEFINITIONS

The term "amyloid beta peptide" means amyloid beta peptides processed from the amyloid beta precursor protein (APP). The most common peptides include amyloid beta peptides 1-40, 1-42, 11-40 and 11-42. Other species less prevalent amyloid beta peptides are described as y-42, whereby y ranges from 2-17, and 1-x whereby x ranges from 24-39 and 41.

The term "carrier" means a non-toxic material used in the formulation of pharmaceutical compositions to provide a medium, bulk and/or useable form to a pharmaceutical composition. A carrier may comprise one or more of such materials such as an excipient, stabilizer, or an aqueous pH buffered solution. Examples of physiologically acceptable carriers include aqueous or solid buffer ingredients including phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counter ions such as sodium; and/or nonionic surfactants such as TWEEN, polyethylene glycol (PEG), and PLURONICS.

The term "compound" is used herein in the context of a "test compound" or a "drug candidate compound" described in connection with the assays of the present invention. As such, these compounds comprise organic or inorganic compounds, derived synthetically or from natural sources. The compounds include inorganic or organic compounds such as polynucleotides, lipids or hormone analogs that are characterized by relatively low molecular weights. Other biopolymeric organic test compounds include peptides comprising from about 2 to about 40 amino acids and larger polypeptides comprising from about 40 to about 500 amino acids, such as antibodies or antibody conjugates.

The term "contact" or "contacting" means bringing at least two moieties together, whether in an in vitro system or an in vivo system.

The term "condition" or "disease" means the overt presentation of symptoms (i.e., illness) or the manifestation of abnormal clinical indicators (e.g., biochemical indicators), resulting from defects in one amyloid beta protein precursor processing. Alternatively, the term "disease" refers to a genetic or environmental risk of or propensity for developing such symptoms or abnormal clinical indicators.

The term "endogenous" shall mean a material that a mammal naturally produces. Endogenous in reference to, for example and not limitation, the term "kinase" shall mean that which is naturally produced by a mammal (for example, and not limitation, a human) or a virus. In contrast, the term non-endogenous in this context shall mean that which is not naturally produced by a mammal (for example, and not limitation, a human) or a virus. Both terms can be utilized to describe both "in vivo" and "in vitro" systems. For example, and not a limitation, in a screening approach, the endogenous or non-endogenous kinase may be in reference to an in vitro screening system. As a further example and not limitation, where the genome of a mammal has been manipulated to include a non-endogenous constitutively activated kinase, screening of a candidate compound by means of an in vivo system is viable.

The term "expression" comprises both endogenous expression and overexpression by transduction.

The term "expressible nucleic acid" means a nucleic acid coding for a proteinaceous molecule, an RNA molecule, or a DNA molecule.

The term "hybridization" means any process by which a strand of nucleic acid binds with a complementary strand through base pairing. The term "hybridization complex" refers to a complex formed between two nucleic acid sequences by virtue of the formation of hydrogen bonds between complementary bases. A hybridization complex may be formed in solution or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed). The term "stringent conditions" refers to conditions that permit hybridization between polynucleotides and the claimed polynucleotides. Stringent conditions can be defined by salt concentration, the concentration of organic solvent, e.g., formamide, temperature, and other conditions well known in the art. In particular, reducing the concentration of salt, increasing the concentration of formamide, or raising the hybridization temperature can increase stringency.

The term "inhibit" or "inhibiting" or "suppress" or "suppressing" or "suppressive," in relationship to the term "response" means that a response is decreased or prevented in the presence of a compound as opposed to in the absence of the compound.

The term "ligand" means an endogenous, naturally occurring molecule specific for an endogenous, naturally occurring receptor.

The term "pharmaceutically acceptable prodrugs or prodrug" as used herein means the prodrugs of the compounds useful in the present invention, which are, within the scope of sound medical judgment, suitable for use in contact with the tissues of patients with undue toxicity, irritation, allergic response commensurate with a reasonable benefit/risk ratio, and effective for their intended use of the compounds of the invention. The term "prodrug" means a compound that is transformed in vivo to yield an effective compound useful in the present invention or a pharmaceutically acceptable salt, hydrate or solvate thereof. The transformation may occur by various mechanisms, such as through hydrolysis in blood. The compounds bearing metabolically cleavable groups have the advantage that they may exhibit improved bioavailability as a result of enhanced solubility and/or rate of absorption conferred upon the parent compound by virtue of the presence of the metabolically cleavable group, thus, such compounds act as pro-drugs. A thorough discussion is provided in Design of Prodrugs, H. Bundgaard, ed., Elsevier (1985); Methods in Enzymology; K. Widder et al, Ed., Academic Press, 42, 309-396 (1985); A Textbook of Drug Design and Development, Krogsgaard-Larsen and H. Bandaged, ed., Chapter 5; "Design and Applications of Prodrugs" 113-191 (1991); Advanced Drug Delivery Reviews, H. Bundgard, 8, 1-38, (1992); J. Pharm. Sci., 77, 285 (1988); Chem. Pharm. Bull., N. Nakeya et al, 32, 692 (1984); Pro-drugs as Novel Delivery Systems, T. Higuchi and V. Stella, 14 A.C.S. Symposium Series, and Bioreversible Carriers in Drug Design, E. B. Roche, ed., American Pharmaceutical Association and Pergamon Press, 1987, which are incorporated herein by reference. An example of the prodrugs is an ester prodrug. "Ester prodrug" means a compound that is convertible in vivo by metabolic means (e.g., by hydrolysis) to an inhibitor compound according to the present invention. For example an ester prodrug of a compound containing a carboxy group may be convertible by hydrolysis in vivo to the corresponding carboxy group.

The term "pharmaceutically acceptable salts or salt" refers to the non-toxic, inorganic and organic acid addition salts, and base addition salts, of compounds of the present invention. These salts can be prepared in situ during the final isolation and purification of compounds useful in the present invention.

The term "pharmaceutical excipients" refers to non-toxic adjuvants or compounds which can be added to the present invention which is capable of enhancing the biologically active effects of the peptide or its absorbancy in the body.

The term "polynucleotide" means a polynucleic acid, in single or double stranded form, and in the sense or antisense orientation, complementary polynucleic acids that hybridize to a particular polynucleic acid under stringent conditions, and polynucleotides that are homologous in at least about 60 percent of its base pairs, and more preferably 70 percent of its base pairs are in common, most preferably 90 percent, and in a special embodiment 100 percent of its base pairs. The polynucleotides include polyribonucleic acids, polydeoxyribonucleic acids, and synthetic analogues thereof. The polynucleotides are described by sequences that vary in length, that range from about 10 to about 5000 bases, optionally about 100 to about 4000 bases, or about 250 to about 2500 bases. An alternate polynucleotide embodiment comprises from about 10 to about 60 bases in length. A alternate embodiment of polynucleotide is the polyribonucleotide of from about 10 to about 22 nucleotides, more commonly described as small interfering RNAs (siRNAs). Another alternate embodiment are nucleic acids with modified backbones such as peptide nucleic acid (PNA), polysiloxane, and 2'-O-(2-methoxy)ethylpho-sphorothioate, or including non-naturally occurring nucleic acid residues, or one or more nucleic acid substituents, such as methyl-, thio-, sulphate, benzoyl-, phenyl-, amino-, propyl-, chloro-, and methanocarbanucleosides, or a reporter molecule to facilitate its detection.

The term "polypeptide" relates to a protein made up of any one of the natural or synthetic amino acids and their equivalents. Common amino acids, for example, are Alanine (Ala), Aspartic acid (Asp), Cysteine (Cys), Glutamic acid (Glu), Phenylalanine (Phe), Glycine (Gly), Histidine (His), Isoleucine (Ile), Lysine, (Lys), Leucine (Leu), Methionine (Met), Asparagine (Asn), Proline (Pro), Glutamine (Gin), Arginine (Arg), Serine (ser), Threonine (Thr), Selenocysteine (Scy), Valine (Val), Tryptophan (Trp), and Tyrosine (Tyr) In the present invention, a polypeptide can mean the amino acid sequence of DAEFRHDSGYEVHHQKLVFFAWDVGSNK-GAIIGLMVGGVVIA (Amyloid beta mutant P22W) (SEQ ID NO:1), DAEFRHDSGYEVHHQKLVFFAEDMGSNK-GAIIGLMVGGVVIA (Amyloid beta mutant P24M) (SEQ ID NO:2), DAEFRHDSGYEVHHQKLVFFAEDGGSNK-GAIIGLMVGGVVIA (Amyloid beta mutant P24G) (SEQ ID NO:3), DAEFRHDSGYEVHHQKLVFFAFDVGSNKGAIIGLMVGGVVIA (Amyloid beta mutant P22F) (SEQ ID NO:4), or DAEFRHDSGYEVHHQKLVFFARDVGSNKGAIIGLMVGGVVIA (Amyloid beta mutant P22R) (SEQ ID NO:5), mutant fragments or biological equivalents thereof. In certain instances, any one of the naturally occurring amino acids can be replaced with a functional amino acid without changing the biological activity of the peptide. For example, peptides are short, sequence- and length-specific oligomers composed of amino acids. These familiar biomolecules are ubiquitous in living cells and assume myriad roles, including cell receptor ligand, endogenous antibiotics, and even components of pulmonary surfactant. Each role assumed by a bioactive peptide will typically correspond to a unique three-dimensional structure. In this way, nature has exquisitely refined bioactive peptide sequences and activities through evolution and, naturally, there has been significant interest in exploiting these molecules as pharmaceutical lead compounds. Often second generation pharmaceutical therapies, have focused on the creation of non-natural peptide mimics containing unnatural amino acids or synthetically modified bases of amino acids. These 'peptidomimetics' can be based on any oligomer that mimics peptide primary structure through use of amide bond isosteres and/or modification of the native peptide backbone, including chain extension or heteroatom incorporation. Peptidomimetic oligomers are often protease-resistant, and may have reduced immunogenicity and improved bioavailability relative to peptide analogues. In addition to primary structural mimicry, a select subset of the sequence-specific peptidomimetic oligomers, the so-called 'foldamers,' exhibits well-defined secondary structural elements such as helices, turns and small, sheet-like structures. When a peptide's bioactivity or its biological equivalent is contingent upon a precise 3-D structure, the capacity of a biomimetic oligomer to fold can be indispensable.

Examples of simple peptidomimetics include azapeptides, oligocarbamates and oligoureas, and common foldamer examples include β-peptides, γ-peptides, oligo(phenylene ethynylene)s, vinylogous sulfonopeptides and poly-N-substituted glycines (peptoids). Therefore, it is within the scope of the present invention that peptidomimetics of the peptide having DAEFRHDSGYEVHHQKLVFFAWDVGSNKGAIIGLMVGGVVIA (Amyloid beta mutant P22W) (SEQ ID NO:1), DAEFRHDSGYEVHHQKLVFFAEDMGSNKGAIIGLMVGGVVIA (Amyloid beta mutant P24M) (SEQ ID NO:2), DAEFRHDSGYEVHHQKLVFFAEDGGSNKGAIIGLMVGGVVIA (Amyloid beta mutant P24G) (SEQ ID NO:3), DAEFRHDSGYEVHHQKLVFFAFDVGSNKGAIIGLMVGGVVIA (Amyloid beta mutant P22F) (SEQ ID NO:4), or DAEFRHDSGYEVHHQKLVFFARDVGSNKGAIIGLMVGGVVIA (Amyloid beta mutant P22R) (SEQ ID NO:5), mutant fragments or biological equivalents thereof and peptidomimetics thereof are clearly within the scope of the present invention and would be obvious to one of ordinary skill in the art.

The term "solvate" means a physical association of a compound useful in this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

The term "subject" includes humans and other mammals including but not limited to murine (mice) rats, rabbit, horse, sheep, bovine, dogs, cats, birds and any other warm blooded animals classified as mammals.

The term "effective amount" or "therapeutically effective amount" means that amount of a compound or agent that will elicit the biological or medical response of a subject that is being sought by a medical doctor or other clinician. In particular, with regard to treating an neuronal disorder, the term "effective amount" is intended to mean that effective amyloid-beta precursor processing inhibiting amount of an compound or agent that will bring about a biologically meaningful decrease in the levels of amyloid beta peptide in the subject's brain tissue or decrease inflammatory response in the subject's brain or subject's body.

The term "treating" means an intervention performed with the intention of preventing the development or altering the pathology of, and thereby alleviating a disorder, disease or condition, including one or more symptoms of such disorder or condition. Accordingly, "treating" refers to both therapeutic treatment and prophylactic or preventative measures. Those in need of treating include those already with the disorder as well as those in which the disorder is to be prevented. The related term "treatment," as used herein, refers to the act of treating a disorder, symptom, disease or condition, as the term "treating" is defined above.

Without further description, it is believed that a person of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLE 1

Dendritic cells (DCs) are the crucial cells providing the necessary components for initiating and developing effective cell-mediated immune (CMI) responses. Dendritic cells, located in most tissues of the body, capture and process Ags, which are then displayed as MHC-peptide complexes on the DC surface. Essential co-stimulatory molecules are upregulated on DCs as they migrate to secondary lymphoid organs (the spleen and lymph nodes) where they liaise with naïve T cells, inducing the activation and proliferation of Ag specific CTLs. Dendritic cell therapy is a relative new approach for disease treatment, but is booming so fast that covers all cancer study. Since CD marker on this type of cell and maturation methods are established recently. DCs vaccine is very viable potential in treatment of varies disease. It has been used in tumor treatment and most effective approach. The safety of DCs vaccine is well documented. There over 90 DCs based vaccine in clinical, adenocarcinoma. However, there is no research report about DCs vaccine in AD. Here, we illustrated our result by using Abeta peptide pulsed DCs as a vaccine in Tg APP/PS1 mice.

Material and Methods:

Peptide preparation: Abeta 1-42 with different mutation were synthesized from Synpep (CA). They are designed as PWT (wild type Abeta1-42), PFM (Abeta with Flemish mutation), PDM (Abeta with Dutch mutation), PFDM (Abeta with both Flemish and Dutch mutation), P22W (Abeta with a new mutation at amino acid 22), P24G (Abeta with mutation at amino acid 24). For details of each peptide see Table 1.

TABLE 1

Comparison of Antigen andH LA differences among Mutations

| Mutation Name | Mutation site (listed aa16-24) | Antigenic Comain (Abeta 1-42) | HLA affinity score |
|---|---|---|---|
| Wild type (PWT) | KLVFFAEDV (SEQ ID NO: 6) | Abeta aa 3-10 and aa 22-29 | 453.27 |
| Flemish mutation (PFM) | KLVFFGEDV (SEQ ID NO: 7) | Abeta aa 3-10 and aa 22-29 | 453.27 |
| Dutch Mutation (PDM) | KLVFFAQDV (SEQ ID NO: 8) | Abeta aa 3-10 and aa 22-29 | 925.042 |
| Flemish plus Dutch (PFDM) | KLVFFGQDV (SEQ ID NO: 9) | Abeta aa 3-10 and aa 22-29 | 925.042 |
| New mutation1 (P22W) | KLVFFAWDV (SEQ ID NO: 10) | Abeta aa 3-10 and aa 22-29 | 6937.812 |
| New mutation2 (P24G) | KLVFFAEDG (SEQ ID NO: 11) | Abeta aa 3-10 and aa 22-29 | 0.486 |

Peptides were diluted with pure DMSO at 10 mg/ml, and then further diluted with culture medium at the working concentration). Mouse rIL4 and rGM-CSF were ordered from BD Pharmgen. BALB/c mouse were ordered from Harland.

Bone Marrow DCs Preparation:

Female BALB/c Mice at 8-12 weeks old were sacrifice mice with CO2, leg bone were removed and placed into dish containing 75-80% Ethanol for 2 minutes maximum. Using a syringe (3 ml with 21 gauge needle), draw up RPMI containing 10% FBS media and switch to smaller needle (25 gauge), so that it will fit inside end of bone. Chop off ends of bones and flush through bones and collected with 50 ml conical tube. Centrifuge cells at 1100 rpm for 10 min at 10° C. and add 3 ml ACK for 30 sec to lyse any RBCs, and then fill tube with 40 ml of HBSS and centrifuge again at 1100 rpm for 10 min at 10° C. Discard supernatant (in hood), and repeat wash by filling tube to 40 ml with HBSS and pellet by centrifuge again.

DCs Culture and Sensitize with Abeta Peptide:

Pour off supernatant and re-suspend to adjust concentration at 1×106 cells/ml, and then plate 3 ml at 1×106 cells/mL into a 6-well culture plate. At 24 hours, aspirate all supernatant to remove all non-adherent cells (lymphocytes, progenitors, etc.) and add back 3 ml of RPMI (10 ng/ml GM-CSF and 10 ng/ml IL-4) containing 10% FBS; On day four, remove 1 ml of culture media and replace with fresh RPMI (10 ng/ml GM-CSF, 10 ng/ml IL-4) containing 10% FBS, and also add Aβ peptide into appropriate wells on day seven to 22.3 ug/ml, just add 0.5-1.0 ml more of fresh RPMI containing 10% FBS to each wells for nutrient purposes. DCs collection and Vaccination: Peptide sensitized DCs were collected and washed with 1×PBS for three times then resuspended at 1×106 cells/ml and injected 300 ul into each mice by tail vein.

Vaccination groups and bleeding procedure: BALB/c mice were grouped at 4 in each group for total 7 groups (6 peptide treated and one control) for this study. They are designated as PWT, PFM, PDM, PFDM, P22W, P24G and DCs control group. 10 days after injection, mice were bled by submandibular phlebotomy with EDTA tube, and plasma were isolated by centrifugation and frozen at −80° C. and booster injections will be given twice monthly with the same amount of antigen.

Antibody titer determination: An ELISA method will be used to determine the antibody levels post vaccination using Abeta1-42 peptide as binding antigen. For determination of plasma anti-Abeta antibody levels from blood taken by submandibular phlebotomy under restrained. 96 well plates will be coated with 50 μl Abeta peptide 1-42 in CBC buffer at 10 μg/ml. A CBC plate was set up for binding background. Then both Abeta and CBC plates were incubated at 4° C. overnight. After 5 washes with wash buffer, plates will be subjected to a blocking step with 180 ul blocking buffer (1×PBS containing 1.5% BSA), then washed an additional 5 times with wash buffer. Samples diluted with blocking buffer will then added into both Abeta plates and CBC-plates, with two-fold serial dilutions starting with 1:50, then incubated at 37° C. for 1 hour, followed by 12 washes with wash buffer. HRP-conjugated anti-mouse IgG were loaded into each well at 1:5000 dilution with dilution buffer, incubated for 1 hour at 37° C., then washed 12 times. TMB substrate will be dissolved in PCB buffer and 100 μl will be added into each well. Colorimetric reaction will be stopped with 25 μl 2N H2SO4. Plates will be read at 450 nm/630 nm, with those samples having readings three times higher than controls being considered as positive and the highest dilution will be the endpoint titer. For any given measure, initial one-way ANOVAs involving all groups will be followed by post hoc pair-by-pair group differences using the Fisher LSD test.

Cytokine expression detection: Cytokine expression profile will be detected by using Bio-Rad Bio-Plex (Bio-Rad, catalogue 171F11181) kits according to the manufacturer's protocol. In brief, allow all reagents to reach room temperature before use and gently mix all liquid reagents prior to use. Pre-wet the Filter-Bottom Microplate by placing 100 μL of Bio-Plex assay buffer into each well and remove the buffer by vacuum filtration.

Vortex the multiplex bead working solution for 15-20 sec at medium speed and add 50 μL into each well. Remove the buffer by vacuum filtration. Wash beads 2× with 100 μL of Bio-Plex wash buffer per well. Blot the plate bottom once with a clean paper. Add 50 μL of diluted standard or sample to the appropriate microplate wells. Cover plate with aluminum foil and place on a microplate shaker with 30 sec incubation at 1100 rpm and then 30 mins at 300 rpm. Remove the solution from wells using vacuum filtration. Wash wells 3 times with 100 μL of Bio-Plex wash buffer per well each time. Blot the plate bottom once with a clean paper after each wash. Vortex the bio-Plex detection antibody working solution gently and add 25 ul to each well. Cover the plate and shake 30 sec at 1100 rpm and 30 mins at 300 rpm at RT. Remove the buffer by vacuum filtration. Wash the plate 3 times with 100 μL of Bio-Plex wash buffer each well each time. Remove the solution by vacuum filtration. Vortex Streptavidin-PE Working Solution vigorously and add 50 ul to each well. Cover plate with aluminum foil and place on a microplate shaker with 30 sec incubation at 1100 rpm and then 10 mins at 300 rpm. Remove the solution by vacuum filtration. Wash beads 3× with 100 μL of Bio-Plex wash buffer per well each time. Blot the plate bottom once with a clean paper. Resuspend the beads in each well with 125 ul of Bio-Plex assay buffer. Cover and shake the plate at 1100 rpm 30 sec immediately before reading the plate on the Bio-Plea system.

Because of the naturally-occurring large variability (100×-1000×) in optical density readings among the various cytokines, optical density readings for each cytokine will be converted to standardized signal intensities. For this conversion, signal mean intensities minus background signal intensity will be determined and standardized to a zero to one scale based on minimum and maximum individual intensity readings for each cytokine. These standardized values will be then used for relative cytokine level comparisons among animal groups.

Epitope mapping: Different Aβ peptide fragments at 20 μg/ml will be used to coat 96 well plates with 50 μl per well. Plate was blocked with 180 μl blocking buffer post coating, then pre and post immune sera will be loaded with serials dilutions. The following step of ELISA will be conducted using the same protocol described for titer assay.

Results:

Anti-Abeta antibody will be the predominant factor to detect in evaluating the success of a vaccine against Abeta. There is no antibody production after two injections of DCs sensitized with wild type Abeta peptide (PWT). However, all other groups that received DCs sensitized with mutant Abeta can induce antibody response even with only one vaccination. The antibody titer can reach as high as 1:16000 with only two inoculations. It is of importance that amount of peptide used for DCs treatment in each injection is as low as 7.4 ug/mice. The antibody level (FIG. 1).

Figure 2:
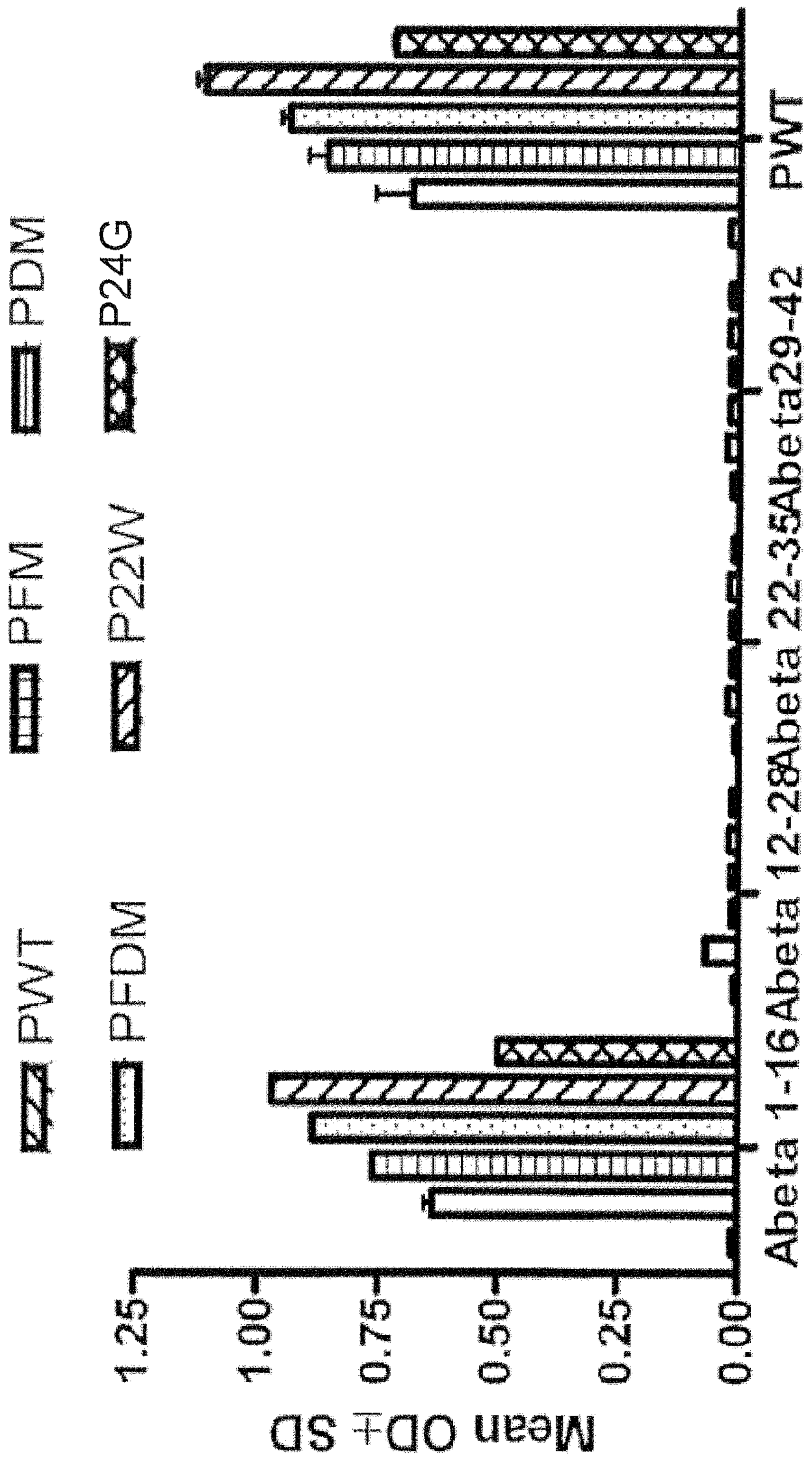
FIG. 2: Epitope mapping result for sera from DCs vaccinated mice. All antisera are mapped at Abeta 1-16. T cell epitope mutation doesn't change the B cell epitope.

Following this result, we further did epitope mapping by using different Abeta peptide fragment to see if there is any epitope change using those peptide sensitized DCs as vaccine (see FIG. 2). Our result indicates all antisera generated from different peptide vaccinated mice bind to PWT and Abeta 1-16, so those mutations only affect antibody response and no epitope switch or alteration.

Figure 3:
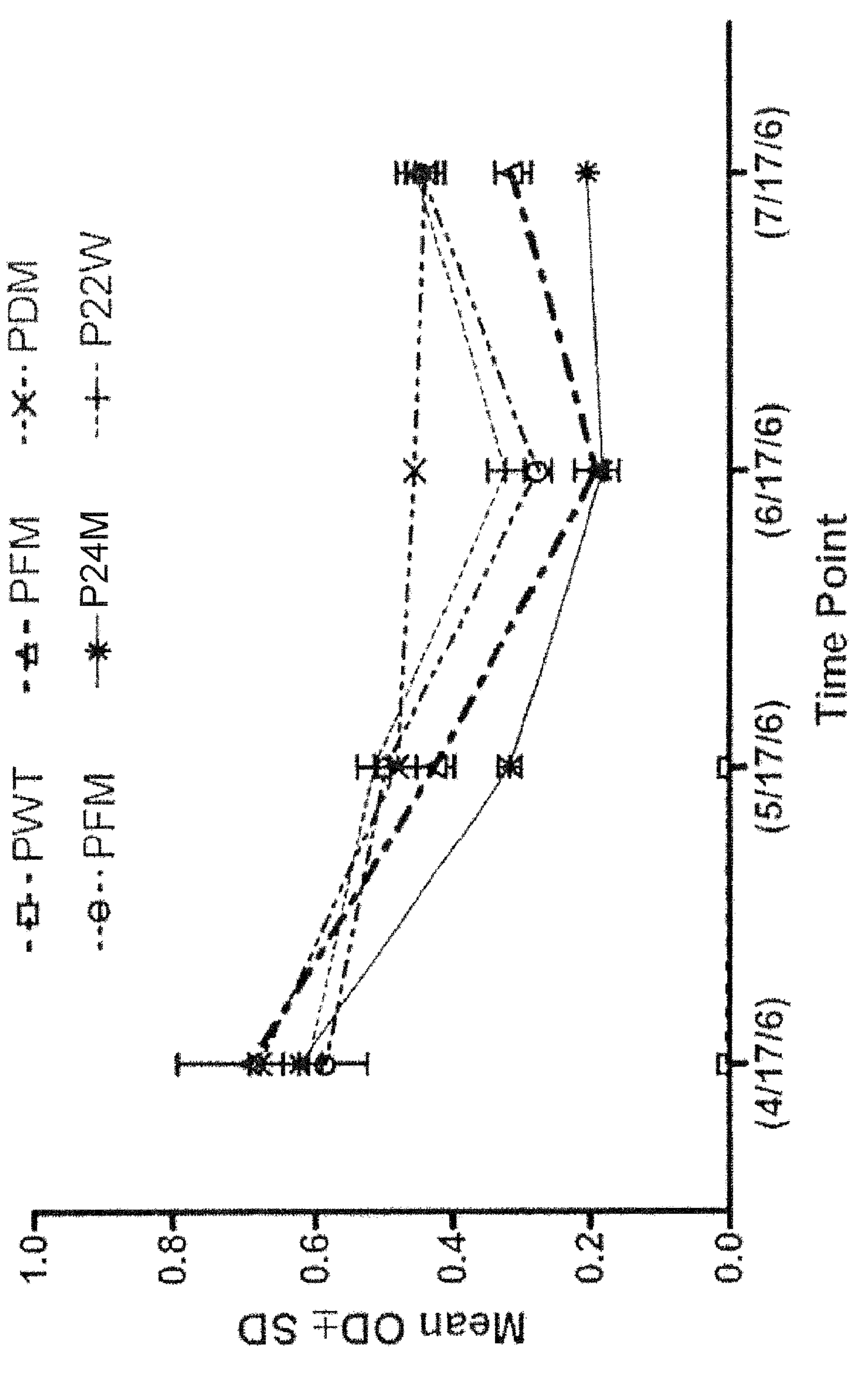
FIG. 3: Antibody duration result of the DCs vaccine. Sera were tested for up to 4 months after the last vaccination and endpoint titer were assayed by ELISA. This result shows there is no significant antibody level decrease within 4 months.

Antibody duration is another important factor in vaccine development. Through time course sampling we found that antibody will last longer than we expected even using such little amount antigen. Our result indicated that the antibody can last at least 4 months (FIG. 3).

Figure 4:
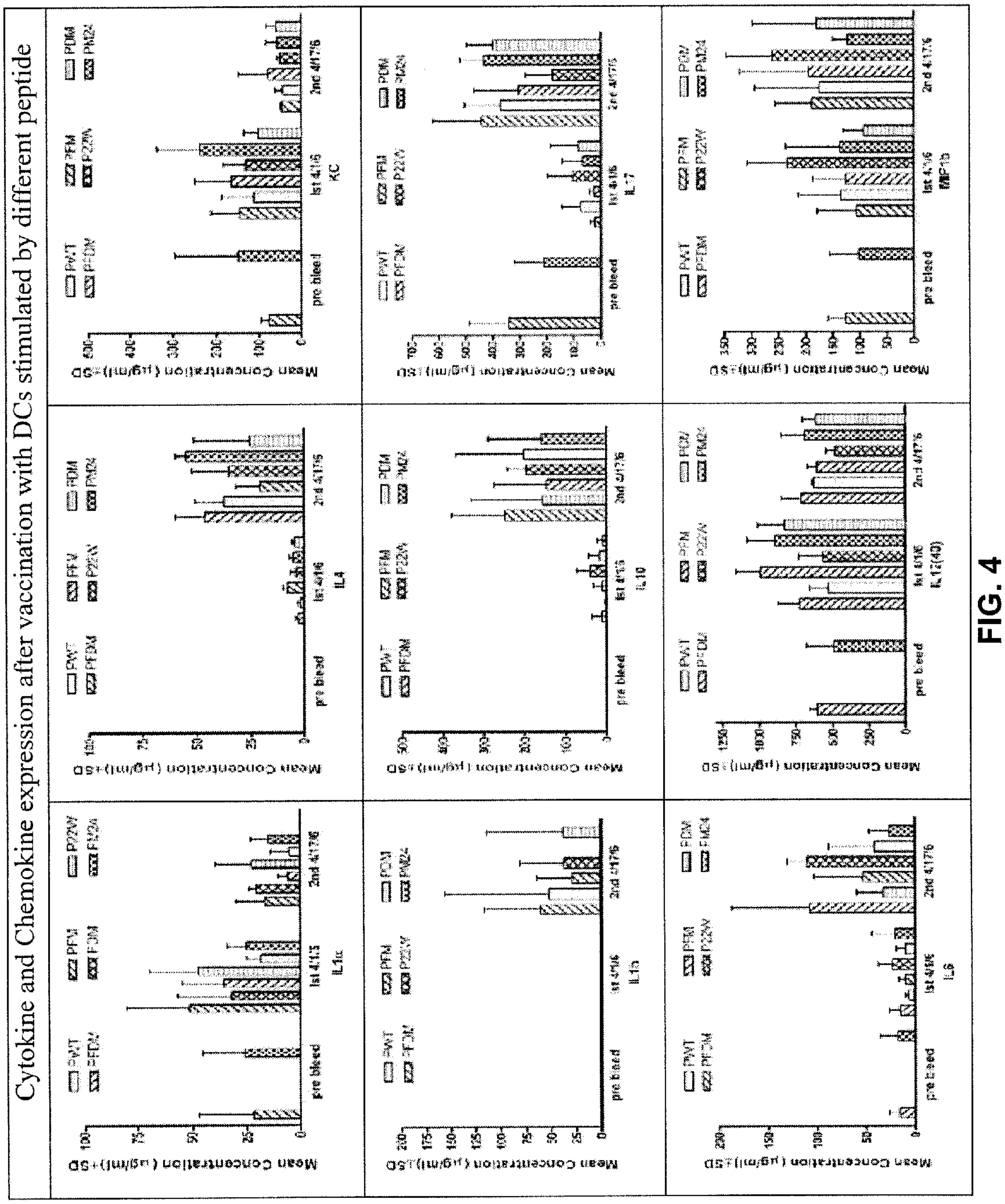
FIG. 4. Cytokine expression file before and after vaccination reveals there is no inflammation cytokine increase significantly. DCs vaccine doesn't induce a global inflammation response.

Inflammation has been considered as the very important safety issue in AD vaccine. Therefore, we have checked the antibody level to these peptide vaccinated mice. There is no difference for both Th1 and Th2 cytokine among all these groups at the same time point ($P>0.05$). It is worth noting that inflammation cytokines like IL1 and TNFα which are considered being related to inflammation didn't increase with antibody level increase. However, Th2 cytokine as IL4 increase with the antibody increasing (See FIG. 4).

Unlike traditional vaccine that use adjuvant to prime the immune response. The unique of DCs vaccine is it requires both antigen presentation and interacted with CD4 T cell. T cell antigen may serve as co-stimulator to facilitate the immune response. It may potent Th0 cell to transform into Th2 cell. T cell antigen located in the Abeta 16-33 (Monsonego et al.) and is highly homology among species (see TABLE 2). Mutant amyloid beta sequences comprised of an amino acid sequence polymers in tandem repeats which making up an entire fragment length of more than 26 amino acid sequence fragment are also contemplated in this patent application. For example, amyloid beta fragment sequence 1-6 in tandem repeats for up to 5 repeats will yield a 30 amino acid length amyloid beta fragment which is distinct from wild-type and which can be used to sensitize DC cells. Any peptide that are at least about 26-42 amino acids or 26-41 amino acids, or 26-40 amino acids or 26-39 amino acids or 26-38 amino acids or 26-37 amino acids or 26-36 amino acids or 26-35 amino acids in length can be used to sensitize DC cells and are contemplated by the present invention. Tables 3 and 4 below are further examples of other types of mutation and fragment lengths that can be used. Further fragments which function as biological equivalents of amyloid beta alleles or peptides can be envisioned as contemplated by one of ordinary skill in the art as taught by the present invention.

TABLE 2

| Species | Amino acid homology of Abeta peptide 1-42 in different species | |
|---|---|---|
| Dog | DAEFRHDSGYEVHHQKLVFFAEDVGSNKGAIIGLMVGGVVIA | (SEQ ID NO: 5) |
| Mouse | DAEF**G**HDSGFEV**R**HQKLVFFAEDVGSNKGAIIGLMVGGVVIA | (SEQ ID NO: 12) |
| Rat | DAEF**G**HDSGFEV**R**HQKLVFFAEDVGSNKGAIIGLMVGGVVIA | (SEQ ID NO: 12) |
| Chinese hamster | DAEF**G**HDSGFEV**R**HQKLVFFAEDVGSNKGAIIGLMVGGVVIA | (SEQ ID NO: 12) |
| Chicken | DAEFRHDSGYEVHHQKLVFFAEDVGSNKGAIIGLMVGGVVIA | (SEQ ID NO: 5) |
| Cattle | DAEFRHDSGYEVHHQKLVFFAEDVGSNKGAIIGLMVGGVVIA | (SEQ ID NO: 5) |
| Monkey | DAEFRHDSGYEVHHQKLVFFAEDVGSNKGAIIGLMVGGVVIA | (SEQ ID NO: 5) |
| Turtle | DAEFRHDSGYFVHHQKLVFFAEDVGSNKGAIIGLMVGGVVIA | (SEQ ID NO: 5) |
| Human | DAEFRHDSGYEVHHQKLVFFAEDVGSNKGAIIGLMVGGVVIA | (SEQ ID NO: 5) |
| Dolphin | DAEFRHDSGYEVHHQKLVFFAEDVGSNKGAIIGLMVGGVVIA | (SEQ ID NO: 5) |
| Bear | DAEFRHDSGYEVHHQKLVFFAEDVGSNKGAIIGLMVGGVVIA | (SEQ ID NO: 5) |
| Bovine | DAEFRHDSGYEVHHQKLVFFAEDVGSNKGAIIGLMVGGVVIA | (SEQ ID NO: 5) |
| Sheep | DAEFRHDSGYEVHHQKLVFFAEDVGSNKGAIIGLMVGGVVIA | (SEQ ID NO: 5) |
| Rabbit | DAEFRHDSGYEVHHQKLVFFAEDVGSNKGAIIGLMVGGVVIA | (SEQ ID NO: 5) |
| Pig | DAEFRHDSGYEVHHQKLVFFAEDVGSNKGAIIGLMVGGVVIA | (SEQ ID NO: 5) |

TABLE 2-continued

| Species | Amino acid homology of Abeta peptide 1-42 in different species | |
|---|---|---|
| Frog | D ***S*** E ***Y*** RHD ***TA*** YEVHHQKLVFEAE ***E*** VGSNKGAIIGLMVGGVVIA | (SEQ ID NO: 13) |
| Fish | ***ET*** E F ***QQ*** D ***SG*** YEVHHQKLVFF ***PK*** DVGSNKGAIIGLMVGGVVIA | (SEQ ID NO: 14) |
| Zebra Fish | ***LRMEAEERHS*** EV ***Y*** HQKLVFFAEDV ***S*** SNKGAIIGLMVGGVVIA | (SEQ ID NO: 15) |

TABLE 3

Abeta peptide fragments 1-25 through 1-35) carrying Dutch mutation sensitized DCs

| Size of pep-tide | Sequences of peptide targeted in PDM | Name of pep-tide our study | SEQ ID NO: |
|---|---|---|---|
| 1-34 | DAEFRHDSGYEVHHQKLVFFA**Q**DVGSNKGAIIGL | PDM34 | 16 |
| 1-33 | DAEFRHDSGYEVHHQKLVFFA**Q**DVGSNKGAIIG | PDM33 | 17 |
| 1-32 | DAEFRHDSGYEVHHQKLVFFA**Q**DVGSNKGAII | PDM32 | 18 |
| 1-31 | DAEFRHDSGYEVHHQKLVEFA**Q**DVGSNKGAI | PDM31 | 19 |
| 1-30 | DAEFRHDSGYEVHHQKLVFFA**Q**DVGSNKGA | PDM30 | 20 |
| 1-29 | DAEFRHDSGYEVHHQKLVFFA**Q**DVGSNKG | PDM29 | 21 |
| 1-28 | DAEFRHDSGYEVHHQKLVFFA**Q**DVGSNK | PDM28 | 22 |
| 1-27 | DAEFRHDSGYEVHHQKLVFFA**Q**DVGSN | PDM27 | 23 |
| 1-26 | DAEFRHDSGYEVHHQKLVFFA**Q**DVGS | PDM26 | 24 |

TABLE 4

Amyloid beta peptides in 35 amino acid length and mutation listed

| Peptide name | Sequence | SEQ ID NO: |
|---|---|---|
| Aβ 1-35) (PWT35) | DAEFRHDSGYEVHHQKLVFFAEDVGSNKGAIIGLM | 25 |
| Aβ 1-35 (PFM35) with Flemish mutation | DAEFRHDSGYEVHHQKLVFFGEDVGSNKGAIIGLM | 26 |
| Aβ 1-35 (PDM35) with Dutch mutation | DAEFRHDSGYEVHHQKLVFFAQDVGSNKGAIIGLM | 27 |
| Aβ 1-35 (PFDM35) with Flemish and Dutch mutation | DAEFRHDSGYEVHHQKLVFFGQDVGSNKGAIIGLM | 28 |
| Aβ 1-35 (PM35) (new mutation) | DAEFRHDSGYEVHHQKLVFFAEAVGSNKGAIIGLM | 29 |

TABLE 4-continued

Amyloid beta peptides in 35 amino acid length and mutation listed

| Peptide name | Sequence | SEQ ID NO: |
|---|---|---|
| Aβ 1-35 (P22W) (new mutation) | DAEFRHDSGYEVHHQKLVFFAEIVGSNKGAIIGLM | 30 |

EXAMPLE 2

It has been theorized that the Alzheimer's disease related inflammation could be a form of autoimmunity that potentially marks a more specific and progressive state of the disease. Preliminary data, such as the measurement of pro-inflammatory cytokines after vaccination with and without adjuvant, suggests that the causes of many of the brain tissue inflammation side effects of the vaccines are possibly due to the adjuvants that carry the antigen. In fact, other studies have shown that adjuvants induce significant pro-inflammatory cytokine expression in vivo including up-regulation of TNF-a, IFNγ, and IL-4 even without being coupled to an antigen.

Our goal is to develop a safer and better Alzheimer Abeta vaccine candidate that will be devoid of the problems associated with current vaccine therapy. Here, we report the successful vaccination of mice with adjuvant-free mutated A β peptides that have significant advantages over both native Abeta and the use of adjuvant.

Material and Methods:

Peptides: Aβ 1-42 and related peptides were obtained from Synpep (Dublin, Calif.). Peptides for vaccination were reconstituted to 10 mg/ml in DMSO and further diluted to 2 mg/ml with phosphate buffered saline.

Mice: 10 weeks old female BALB/c mice from the Jackson laboratories were housed in Varian standard cages including amber igloos and vaccinated when 14 weeks old. A total of 28 mice were grouped into 7 vaccination groups each with four animals. Differently mutated Aβ1-42 peptides were used for each group and a 1×PBS (also containing 10% DMSO) as a control group. Initial subcutaneous vaccination began at 100 μg peptide in 100 μl VEHICLE and subsequent booster vaccinations proceeded at 100 μg peptide (100 μl) at two weeks intervals. A third inoculation was carried out with 50 μg peptide in 100 μl.

Bleeding and plasma collection procedures: 10 days after injection, mice were bled by submandibular phlebotomy into EDTA tubes, and plasma was separated by centrifugation at 1500 g for 20 minutes with StatSampler from StatSpin (MA). Plasma were isolated by centrifugation and frozen at −80° C.

Antibody titer determination: Anti-amyloid beta antibody (6E10) was purchased from Signet Laboratories (Dedham, Mass.) and used as positive control. Antibody levels post vaccination was assayed by ELISA using Abeta1-42 peptide as binding antigen. In brief, 96 well plates were coated with 50 μl Abeta peptide 1-42 in CBC buffer at 10 μg/ml. A CBC plate was set up for binding background, and then both Abeta and CBC plates were incubated at 4° C. overnight. After 5 washes, plates were subjected to a blocking step with 180 μl blocking buffer (1×PBS containing 1.5% BSA), and incubated for 1 hour at 37° C., then washed for an additional 5 times with wash buffer. Samples, diluted with blocking buffer, were added to both Abeta plates and CBC-plates, with two-fold serial dilutions starting at 1:100, incubated at 37° C. for 1 hour, followed by 12 washes with wash buffer. HRP-conjugated anti-mouse IgG (Sigma Alderich) was loaded into each well at 1:5000 dilution, incubated for 1 hour at 37° C., and then washed 12 times. TMB peroxidase substrate was dissolved in PCB buffer and 100 μl were added to each well. The colorimetric reaction was stopped with 25 μl 2N H2SO4. Plates were read at 450 nm/630 nm, and samples with readings three times higher than controls were considered positive. The highest dilution was used as endpoint titer.

Cytokine expression detection: The Cytokine expression profiles were determined using the Bio-Rad Bio-Plex kits (Bio-Rad, catalogue 171F11181). Samples and standards were prepared using company protocols with the initial concentration of standards ranging from 32,000 pg/ml to 1.95 pg/ml. The plasma samples were prepared for analysis by diluting 1 volume of the sample with 3 volumes of the Bio-Plex mouse sample diluent. Wells on 96-well filter plate were pre-wet with 100 μl of Bio-Plex assay buffer. The buffer was removed by vacuum filtration. The multiplex bead working solution was vortexed for 15-20 sec at medium speed and 50 ul was pipetted into each well. In each well, 100 μl of Bio-Plex wash buffer was pipetted and then removed by vacuum filtration. 50 μl of diluted standard or sample was added into each well. The plate was covered with aluminum foil and placed onto a microplate shaker. At the end of the first incubation, the reagents were removed by vacuum filtration. The wash step followed as previously mentioned and repeated 3 times. The buffer was removed by vacuum filtration after every wash. The Bio-Plex detection antibody working solution was vortexed gently and 25 was added to each well. The entire plate was then covered with a new sheet of sealing tape. The plate was covered with foil and incubated at room temperature with shaking for 30 minutes. The sealing tape was discarded and the liquid removed by vacuum filtration. The wash step followed as previously mentioned and repeated 3 times with filtration and blotting following each wash. The 1× streptavidin-PE was vigorously vortexed and 50 μl was pipetted into each well. The plate was covered with sealing tape and foil to be incubated at room temperature with shaking as previously mentioned for 10 minutes. At the end of the 10 min incubation, the sealing tape was discarded and the liquid removed by vacuum filtration. Wash steps were repeated three times followed by filtration and blotting after each wash. The beads were then resuspended in each well with 125 μl of Bio-Plex assay buffer. Immediately before reading the plate on the Bio-Plex system, the plate was covered with a new sheet of sealing tape and incubated at room temperature with shaking for 30 seconds. Because of the naturally-occurring variability of cytokine levels, optical density readings for each cytokine were normalized to a 0-1 scale that was used to compare animal groups.

Epitope mapping: Different Abeta peptide fragments (Abeta 1-16, 12-28, 22-35, and 29-42) as well as PWT at 20 μg/ml was used to coat 96 well plates with 50 μl per well. The plate was blocked with 180 μl blocking buffer post coating and pre and post immune sera were loaded with serials dilutions. The following step of ELISA will be conducted using the same protocol described for titer assay.

Figure 5A:
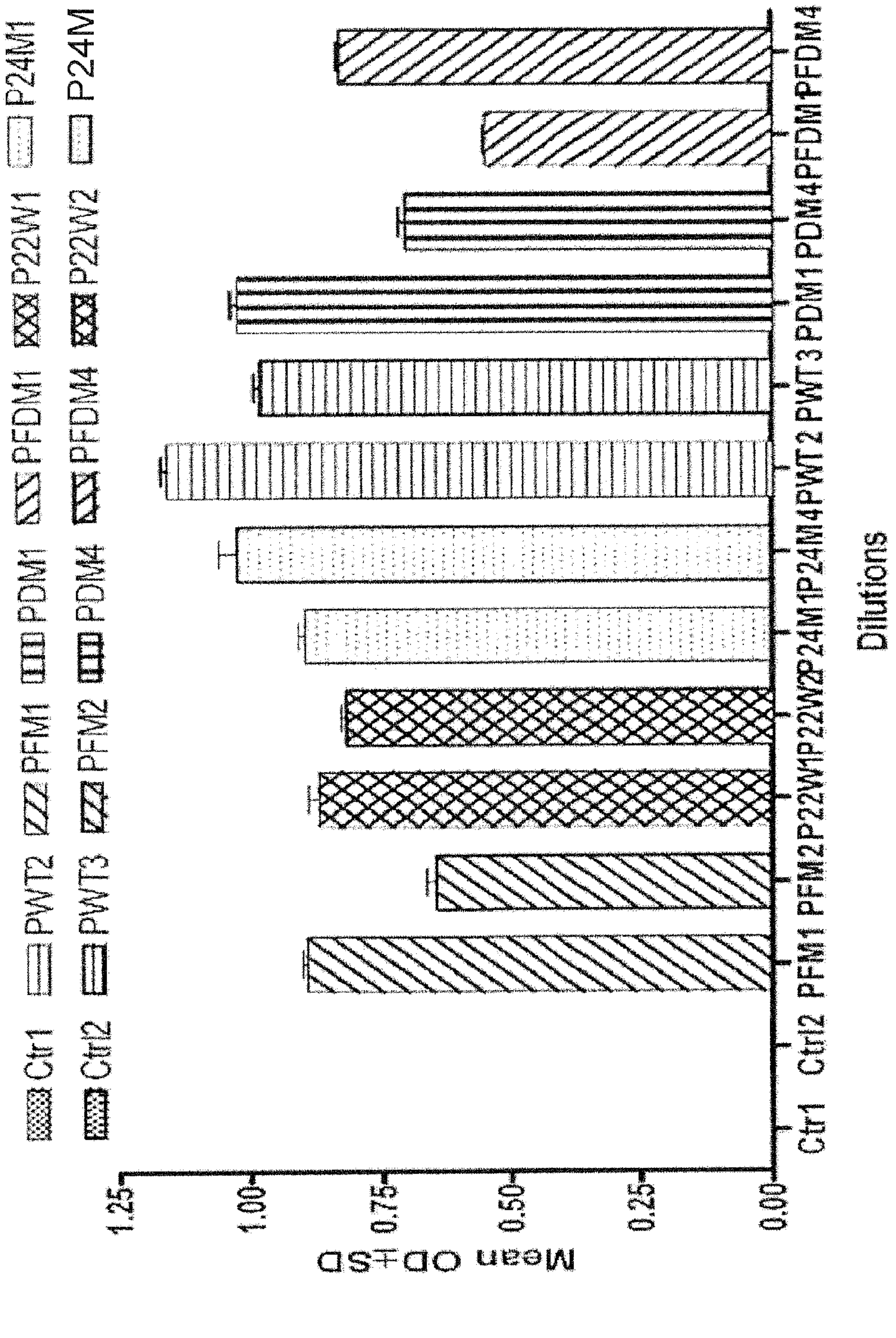
FIG. 5. ELISA results for antibody detection at 1:1024 dilution.
Figure 5B:
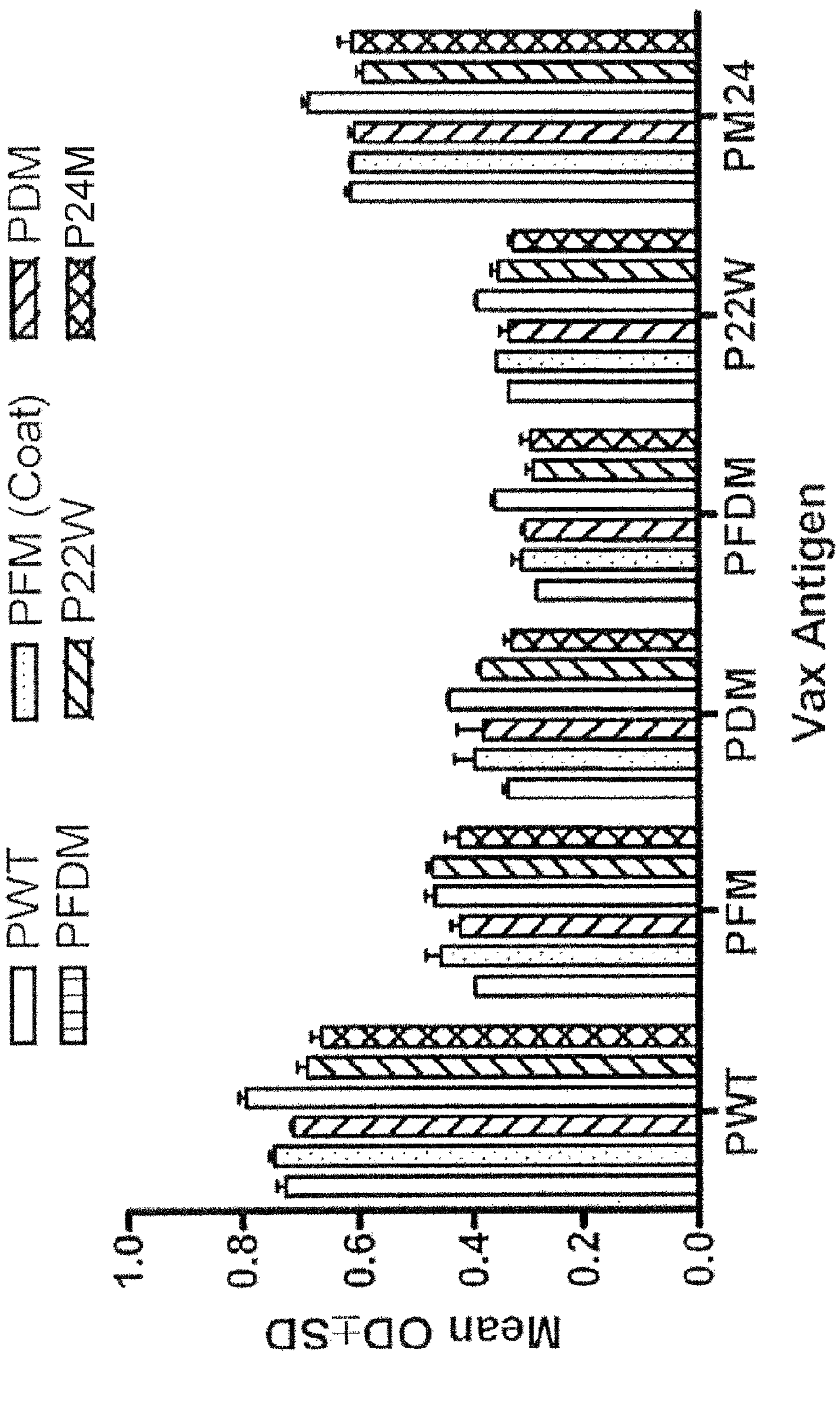

Results:

Antibody Response after vaccination: We recently reported that mutations in the Abeta 1-42 peptide can change the antigenicity of the peptide. We have now designed Abeta peptides with new mutations of the T cell epitope and used them as vaccines without adjuvant. Mice vaccinated with various mutated Abeta 1-42 peptides induce antibody responses after two inoculations, while no antibody can be detected in the control group (FIG. 5A). All antibodies induced by the peptide injection bind to the same epitope. There is no difference in recognition between the various anti-sera and peptides such that all anti-sera recognize the 1-16 epitope on all peptides (FIG. 5B)

Figure 6:
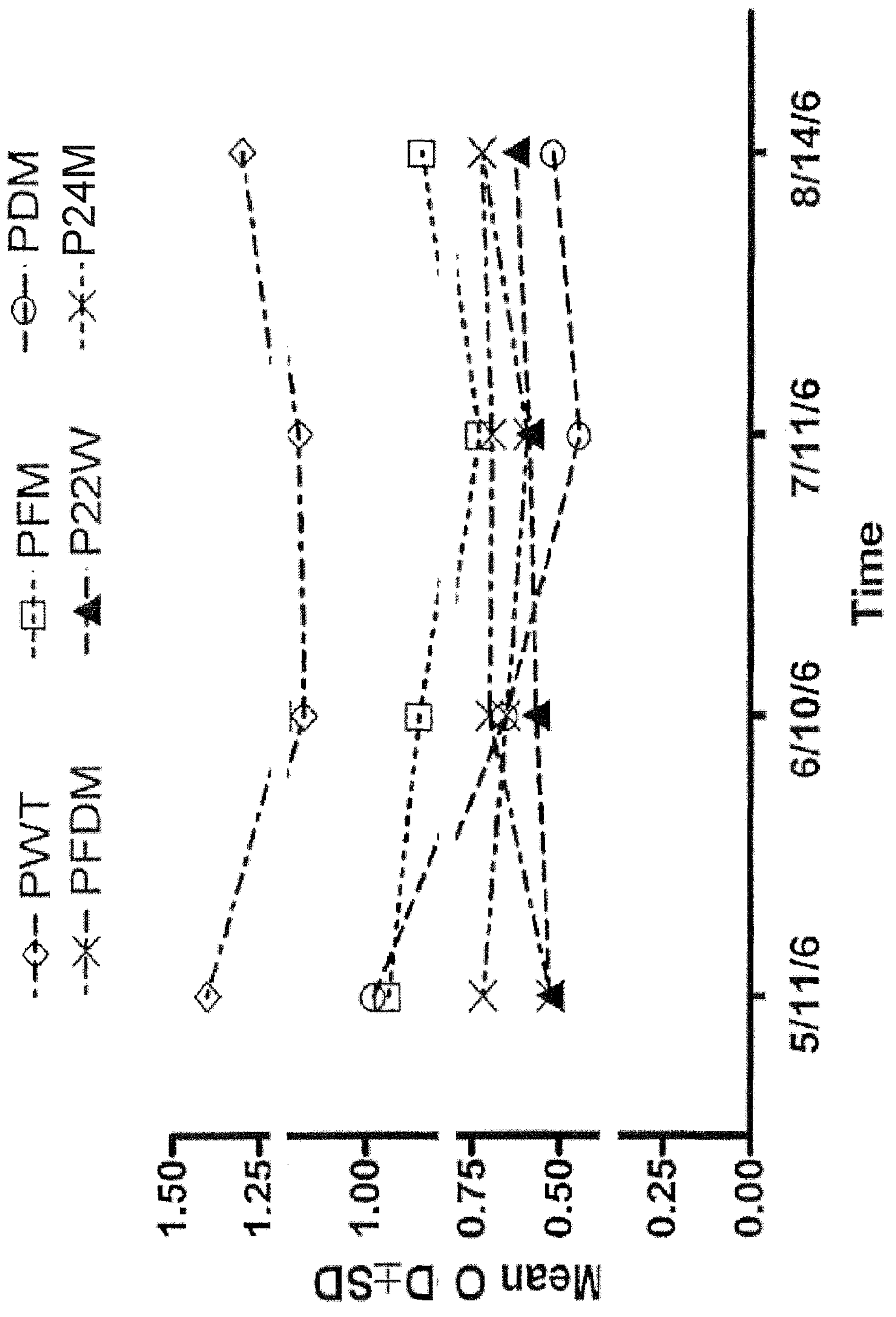
FIG. 6. Shows the antibody duration detected by ELISA after three inoculations at 1:2048 dilutions. We have randomly picked up a mouse from each group and collected sera monthly base for up to six months. There were no significant reductions even six months after vaccination.

Antibody duration was evaluated for all vaccinated mice and one mouse of each group was selected for continuous monitoring of the antibody titer. We show that after three inoculations of an Abeta peptide without adjuvant mice can produce antibodies for up to 6 months. (FIG. 6).

Figure 7:
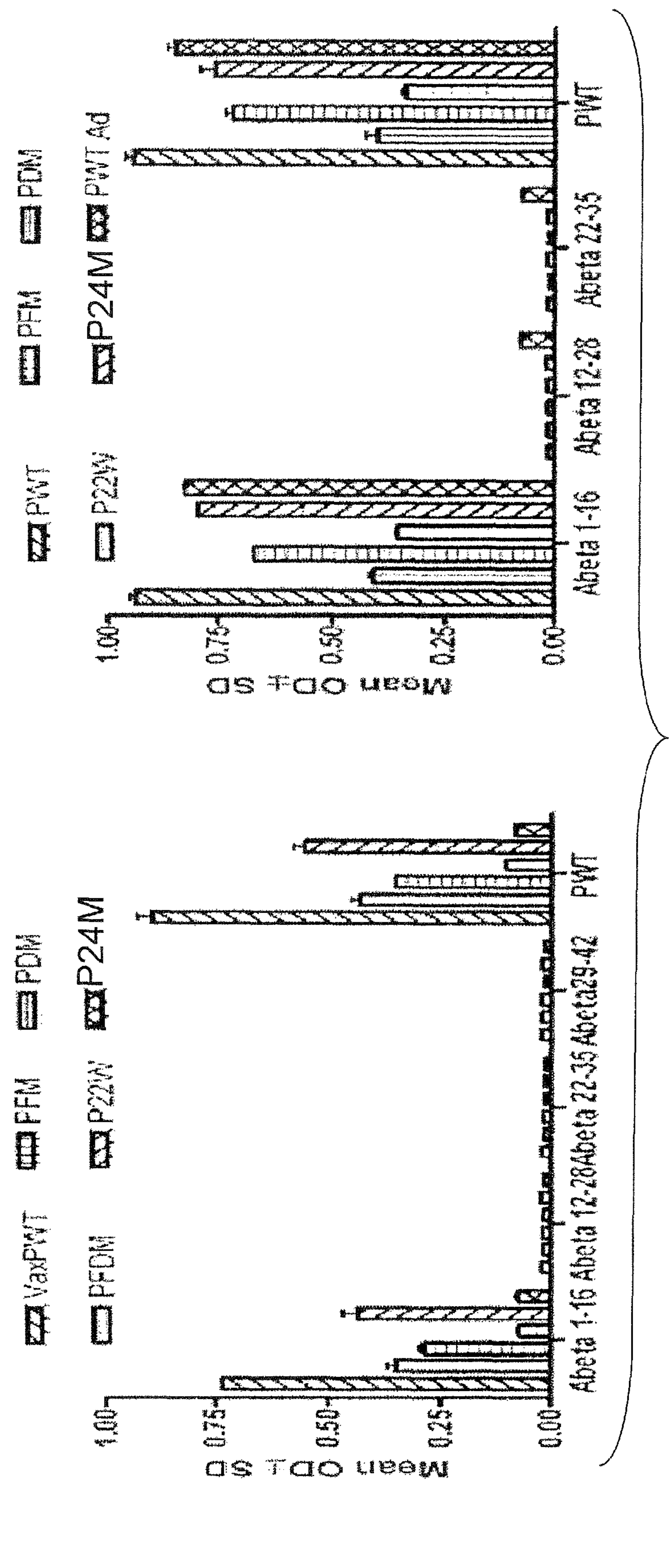
FIG. 7. Results of epitope mapping by using ELISA with Abeta peptide fragment as capture antigen. Anti-sera from mice vaccinated with peptide without adjuvant are designated as the antigen used for vaccination. Left panel showed that all anti-sera bind to Abeta 1-16 as well as Abeta 1-42. There is no epitope switching occurred while with the T cell epitope mutant peptide as antigen. Right panel is the comparison of PWT vaccination with and with out adjuvant. The result shows that adjuvant has no effects on epitopes.

One of the major concerns regarding vaccination with mutated peptides is epitope switching. This implies that there is no epitope change induced by the mutations. Also, does this need to go here. Your data needs to be presented as answers to a logical progression of questions In addition it needs to be shown that the exposure of epitopes is not affected by the presence or absence of adjuvant. To this end, we mapped the epitopes in ELISA assays with different Abeta fragments and antisera generated from our vaccine study. Our results show that all peptides in the presence or absence of adjuvant expose the same epitope (FIG. 7).

Figure 8:
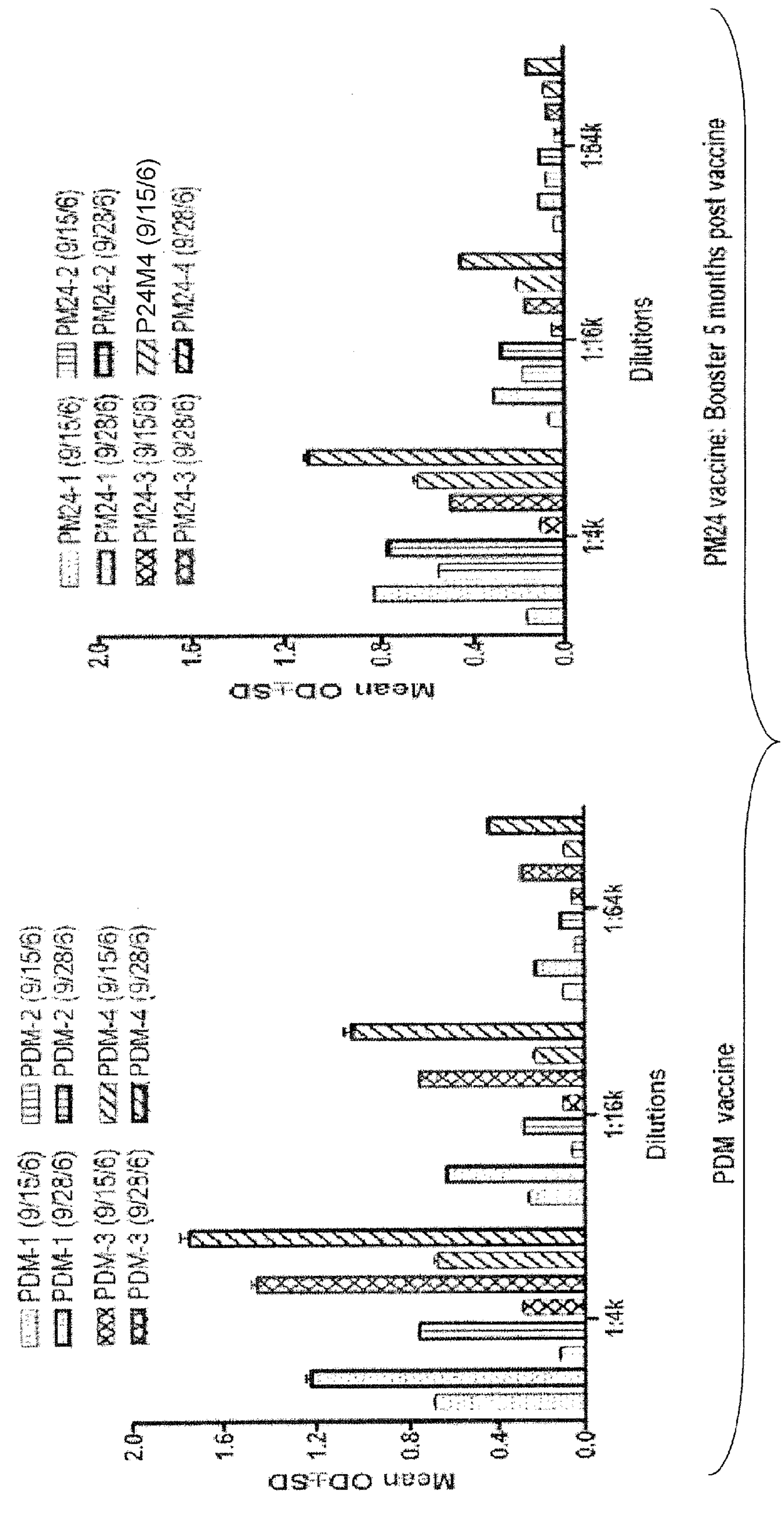
FIG. 8. ELISA results show the antibody level after 6 months is still greater than 1:64 K, and can be further stimulated after boost with 50 ug antigen dose per mice.

Six months later post the third inoculation, two groups of mice, PDM and PM24, were boosted with 50 ug/mice. Then antibodies were tested by ELISA post 10 days of vaccination. The result indicated the even without adjuvant this Abeta peptide itself can induce long term antibody response and with a good memory response. (See FIG. 8).

Figure 9:
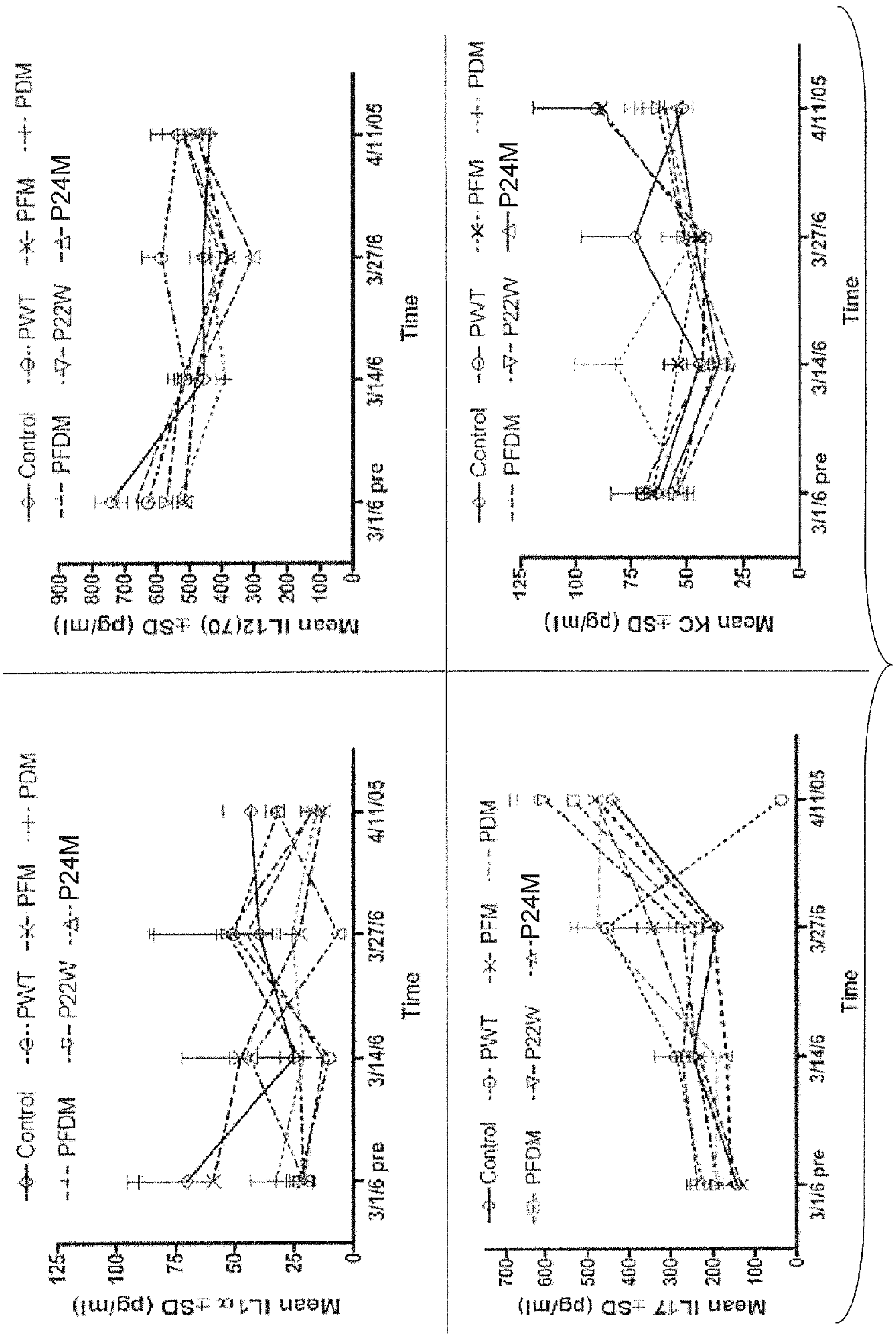
FIG. 9. Demonstrates that the cytokine level at different time point generated by using Bio-Plex. There are no significant differences among all peptides and time points for all inflammation related cytokines. However, some cytokine do change with time course, such as IL-17, and correlated to the antibody change.

One of the main reasons for the suspension of vaccination clinical trials is the development of inflammation in the participating subject and this problem was severe in a few subjects receiving the AN1792 Abeta vaccine. To test for inflammation in the vaccinated mice, we generated Bio-Plex cytokine expression profiles of all mice. Levels varied consistently, between the groups of vaccinated mice and sham controls as well as mice that had been vaccinated with wild-type versus mutated Abeta peptide. The profile for each vaccinated mouse indicated a normal T-cell immune response with elevated Th1 and Th2 associated cytokines. Based on our cytokine expression profile we did not detect any markers of pro-inflammation or any up-regulation of cytokines and chemokines associated with inflammatory immune response (FIG. 9).

Figure 10:
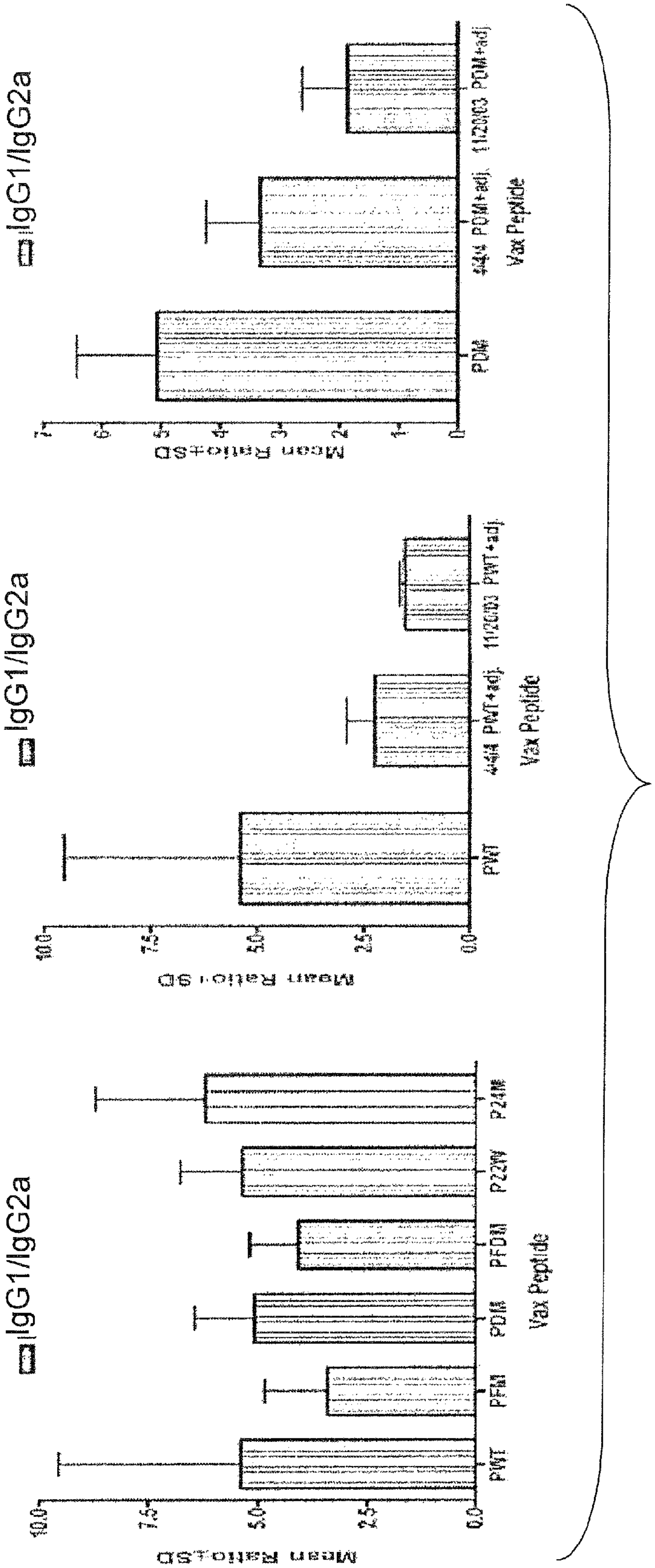
FIG. 10. Antibody isotyping shows that most of these peptides cause a tendency towards an IgG1 antibody response, such as P24M, P22W. Some of elicits an IgG2a response, like PFM and PFDM. There are no significant differences among all peptides (n=4, P>0.05). However, when no adjuvant vaccines are compared to adjuvant treated vaccine, adjuvant MPL treated vaccine induces a Th1 response. Graph in the middle illustrates the trends of a typical Th1 response by adjuvant in PWT vaccination. (n=4, P>0.05); Panel left is PDM antigen showing that adjuvant clearly induces a Th1 response. (n=4, P<0.05).
Figure 11:
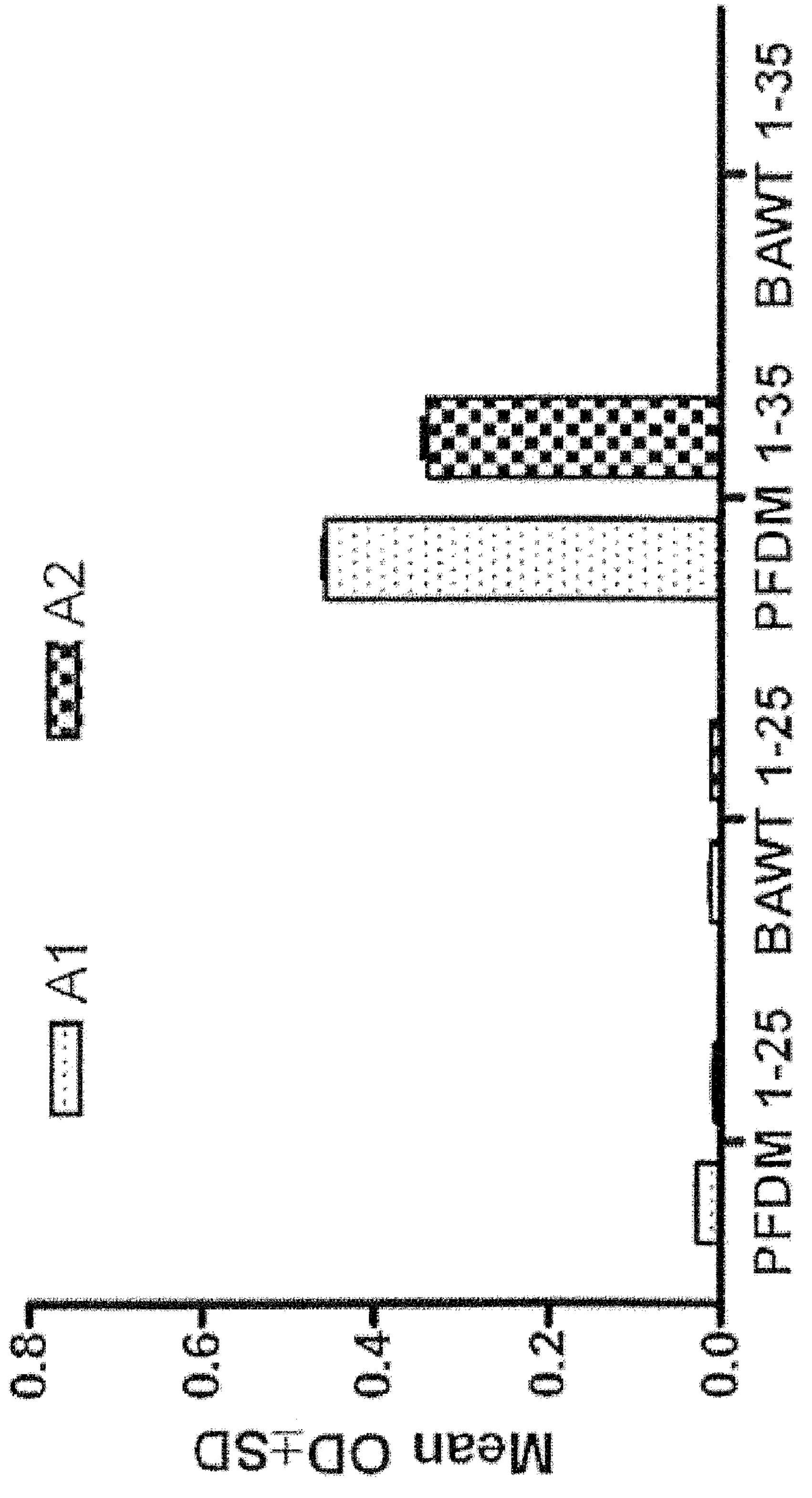
FIG. 11. Mapping result of T cell epitope with Abeta fragment carrying Dutch mutation by ELISA. As indicated in the above graph, there is no antibody production after two vaccinations with Abeta 1-25, 1-35 and Abeta 1-25 carrying Dutch mutation (1×106 cells/mice, treated with 20 μg/million cell). However, there is antibody production in the group that received DCs treated with Abeta 1-35 carrying Dutch mutation (1:800 dilutions).

To further confirm the inflammation issue, we detected type one and type two T cell response by using the mouse anti-Abeta IgG isotyping method. Our result revealed that major type of anti-Abeta antibody is IgG1 (except P22W and PDM), so this no adjuvant method induces Th2 response. (see FIG. 10).

Overall, the process of developing a highly immunogenic peptide to be used for vaccination without the assistance and interference of an adjuvant complex is a novel and ideal process for vaccine development. Results presented here demonstrate definite advantages over previous vaccination protocols, which strongly support our Adjuvant-Free Vaccine Hypothesis. The data clearly show that wild type and mutated amyloid beta peptide administrated without adjuvant induce a strong and long lasting antibody response. While previous studies suggested that adjuvant-free vaccination might help induce pathways of autoimmunity, we report the first use of adjuvant-free Abeta as Alzheimer's vaccines and demonstrate that T cell epitope mutation will contribute to either Th1 or Th2 response. Those peptides will have an outstanding promise for the treatment of Alzheimer's disease.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference

What is claimed is:

1. An isolated peptide comprising an amino acid sequence selected from among DAEFRHDSGYEVHHQKLVFFAWDVGSNKGAIIGLMVGGVVIA (Amyloid beta mutant P22W) (SEQ ID NO:1), DAEFRHDSGYEVHHQKLVFFAEDMGSNKGAIIGLMVGGVVIA (Amyloid beta mutant P24M) (SEQ ID NO:2), DAEFRHDSGYEVHHQKLVFFAEDGGSNKGAIIGLMVGGVVIA (Amyloid beta mutant P24G) (SEQ ID NO:3), DAEFRHDSGYEVHHQKLVFFAFDVGSNKGAIIGLMVGGVVIA (Amyloid beta mutant P22F) (SEQ ID NO:4), or DAEFRIIDSGYEVHHQKLVFFARDVGSNKGAIIGLMVGGVVIA (Amyloid beta mutant P22R) (SEQ ID NO:5).

2. The isolated peptide of claim 1, wherein said peptide consists of an amino acid sequence selected from among DAEFRHDSGYEVHHQKLVFFAWDVGSNKGAIIGLMVGGVVIA (Amyloid beta mutant P22W) (SEQ ID NO:1), or DAEFRHDSGYEVHHQKLVFFAEDMGSNKGAIIGLMVGGVVIA (Amyloid beta mutant P24M) (SEQ ID NO:2), or DAEFRHDSGYEVHHQKLVFFAEDGGSNKGAIIGLMVGGVVIA (Amyloid beta mutant P24G) (SEQ ID NO:3), or DAEFRHDSGYEVHHQKLVFFAFDVGSNKGAIIGLMVGGVVIA (Amyloid beta mutant P22F) (SEQ ID NO:4), or DAEFRHDSGYEVHHQKLVFFARDVGSNKGAIIGLMVGGVVIA (Amyloid beta mutant P22R) (SEQ ID NO:5).

3. The isolated peptide of claim 1, wherein said peptide comprises the amino acid sequence: DAEFRHDSGYEVHHQKLVFFAWDVGSNKGAIIGLMVGGVVIA (Amyloid beta mutant P22W) (SEQ ID NO:1).

4. The isolated peptide of claim 1, wherein said peptide comprises the amino acid sequence: DAEFRHDSGYEVHHQKLVFFAEDMGSNKGAIIGLMVGGVVIA (Amyloid beta mutant P24M) (SEQ ID NO:2).

5. The isolated peptide of claim 1, wherein said peptide comprises the amino acid sequence: DAEFRHDSGYEVHHQKLVFFAEDGGSNKGAIIGLMVGGVVIA (Amyloid beta mutant P24G) (SEQ ID NO:3).

6. The isolated peptide of claim 1, wherein said peptide comprises the amino aid sequence: DAEFRHDSGYEVHHQKLVFFAFDVGSNKGAIIGLMVGGVVIA (Amyloid beta mutant P22F) (SEQ ID NO:4).

7. The isolated peptide claim 1, wherein said peptide comprises the amino acid sequence: DAEFRHDSGYEVH- HQKLVFFARDVGSNKGAIIGLMVGGVVIA (Amyloid beta mutant P22R) (SEQ ID NO:5).

8. The isolated peptide of claim 1, wherein said peptide consists of the amino acid sequence: DAEFRHDSGYEVHHQKLVFFAWDVGSNKGAIIGLMVGGVVIA (Amyloid beta mutant P22W) (SEQ ID NO:1).

9. The isolated peptide of claim 1, wherein said peptide consists of the amino acid sequence: DAEFRHDSGYEVHHQKLVFFAEDMGSNKGAIIGLMVGGVVIA (Amyloid beta mutant P24M) (SEQ ID NO:2).

10. The isolated peptide of claim 1, wherein said peptide consists of the amino acid sequence: DAEFRHDSGYEVHHQKLVFFAEDGGSNKGAIIGLMVGGVVIA (Amyloid beta mutant P24G) (SEQ ID NO:3).

11. The isolated peptide of claim 1, wherein said peptide consists of the amino acid sequence: DAEFRHDSGYEVHHQKLVFFAFDVGSNKGAIIGLMVGGVVIA (Amyloid beta mutant P22F) (SEQ ID NO:4).

12. The isolated peptide claim 1, wherein said peptide consists of the amino acid sequence: DAEFRHDSGYEVHHQKLVFFARDVGSNKGAIIGLMVGGVVIA (Amyloid beta mutant P22R) (SEQ ID NO:5).

13. A pharmaceutical composition comprising a peptide and a pharmaceutically acceptable carrier or pharmaceutical excipient, wherein said peptide comprises an amino acid sequence selected from among DAEFRHDSGYEVHHQKLVFFAWDVGSNKGAIIGLMVGGVVIA (Amyloid beta mutant P22W) (SEQ ID NO:1), DAEFRHDSGYEVHHQKLVFFAEDMGSNKGAIIGLMVGGVVIA (Amyloid beta mutant P24M) (SEQ ID NO:2), DAEFRHDSGYEVHHQKLVFFAEDGGSNKGAIIGLMVGGVVIA (Amyloid beta mutant P24G) (SEQ ID NO:3), DAEFRHDSGYEVHHQKLVFFAFDVGSNKGAIIGLMVGGVVIA (Amyloid beta mutant P22F) (SEQ ID NO:4), or DAEFRHDSGYEVHHQKLVFFARDVGSNKGAIIGLMVGGVVIA (Amyloid beta mutant P22R) (SEQ ID NO:5).

14. The pharmaceutical composition of claim 13, wherein said peptide consists of an amino acid sequence selected from among DAEFRHDSGYEVHHQKLVFFAWDVGSNKGAIIGLMVGGVVIA (Amyloid beta mutant P22W) (SEQ ID NO:1), or DAEFRHDSGYEVHHQKLVFFAEDMGSNKGAIIGLMVGGVVIA (Amyloid beta mutant P24M) (SEQ ID NO:2), or DAEFRHDSGYEVHHQKLVFFAEDGGSNKGAIIGLMVGGVVIA (Amyloid beta mutant P24G) (SEQ ID NO:3), or DAEFRHDSGYEVHHQKLVFFAFDVGSNKGAIIGLMVGGVVIA (Amyloid beta mutant P22F) (SEQ ID NO:4), or DAEFRHDSGYEVHHQKLVFFARDVGSNKGAIIGLMVGGVVIA (Amyloid beta mutant P22R) (SEQ ID NO:5).

15. A kit comprising a peptide and a pharmaceutically acceptable carrier or pharmaceutical excipient, wherein said peptide comprises an amino acid sequence selected from among DAEFRHDSGYEVHHQKLVFFAWDVGSNKGAIIGLMVGGVVIA (Amyloid beta mutant P22W) (SEQ ID NO:1), DAEFRHDSGYEVHHQKLVFFAEDMGSNKGAIIGLMVGGVVIA (Amyloid beta mutant P24M) (SEQ ID NO:2), DAEFRHDSGYEVHHQKLVFFAEDGGSNKGAIIGLMVGGVVIA (Amyloid beta mutant P24G) (SEQ ID NO:3), DAEFRHDSGYEVHHQKLVFFAFDVGSNKGAIIGLMVGGVVIA (Amyloid beta mutant P22F) (SEQ ID NO:4), or DAEFRHDSGYEVHHQKLVFFARDVGSNKGAIIGLMVGGVVIA (Amyloid beta mutant P22R) (SEQ ID NO:5).

16. The kit of claim 15, wherein said peptide consists of an amino acid sequence selected from among DAEFRHDSGYEVHHQKLVFFAWDVGSNKGAIIGLMVGGVVIA (Amyloid beta mutant P22W) (SEQ ID NO:1), or DAEFRHDSGYEVHHQKLVFFAEDMGSNKGAIIGLMVGGVVIA (Amyloid beta mutant P24M) (SEQ ID NO:2), or DAEFRHDSGYEVHHQKLVFFAEDGGSNKGAIIGLMVGGVVIA (Amyloid beta mutant P24G) (SEQ ID NO:3), or DAEFRHDSGYEVHHQKLVFFAFDVGSNKGAIIGLMVGGVVIA (Amyloid beta mutant P22F) (SEQ ID NO:4), or DAEFRHDSGYEVHHQKLVFFARDVGSNKGAIIGLMVGGVVIA (Amyloid beta mutant P22R) (SEQ ID NO:5).

17. An isolated polynucleotide comprising a nucleic acid sequence encoding a peptide comprising an amino acid sequence selected from among DAEFRHDSGYEVHHQKLVFFAWDVGSNKGAIIGLMVGGVVIA (Amyloid beta mutant P22W) (SEQ ID NO:1), DAEFRHDSGYEVHHQKLVFFAEDMGSNKGAIIGLMVGGVVIA (Amyloid beta mutant P24M) (SEQ ID NO:2), DAEFRHDSGYEVHHQKLVFFAEDGGSNKGAIIGLMVGGVVIA (Amyloid beta mutant P24G) (SEQ ID NO:3), DAEFRHDSGYEVHHQKLVFFAFDVGSNKGAIIGLMVGGVVIA (Amyloid beta mutant P22F) (SEQ ID NO:4), or DAEFRHDSGYEVHHQKLVFFARDVGSNKGAIIGLMVGGVVIA (Amyloid beta mutant P22R) (SEQ ID NO:5).

18. The isolated polynucleotide of claim 17, wherein said peptide consists of an amino acid sequence selected from among DAEFRHDSGYEVHHQKLVFFAWDVGSNKGAIIGLMVGGVVIA (Amyloid beta mutant P22W) (SEQ ID NO:1), or DAEFRHDSGYEVHHQKLVFFAEDMGSNKGAIIGLMVGGVVIA (Amyloid beta mutant P24M) (SEQ ID NO:2), or DAEFRHDSGYEVHHQKLVFFAEDGGSNKGAIIGLMVGGVVIA (Amyloid beta mutant P24G) (SEQ ID NO:3), or DAEFRHDSGYEVHHQKLVFFAFDVGSNKGAIIGLMVGGVVIA (Amyloid beta mutant P22F) (SEQ ID NO:4), or DAEFRHDSGYEVHHQKLVFFARDVGSNKGAIIGLMVGGVVIA (Amyloid beta mutant P22R) (SEQ ID NO:5).

19. A method of treating Alzheimer's in a mammal, comprising administering an effective amount of a peptide to the mammal, wherein the peptide comprises an amino acid sequence selected from among DAEFRHDSGYEVHHQKLVFFAWDVGSNKGAIIGLMVGGVVIA (Amyloid beta mutant P22W) (SEQ ID NO:1), DAEFRHDSGYEVHHQKLVFFAEDMGSNKGAIIGLMVGGVVIA (Amyloid beta mutant P24M) (SEQ ID NO:2), DAEFRHDSGYEVHHQKLVFFAEDGGSNKGAIIGLMVGGVVIA (Amyloid beta mutant P24G) (SEQ ID NO:3), DAEFRHDSGYEVHHQKLVFFAFDVGSNKGAIIGLMVGGVVIA (Amyloid beta mutant P22F) (SEQ ID NO:4), or DAEFRHDSGYEVHHQKLVFFARDVGSNKGAIIGLMVGGVVIA (Amyloid beta mutant P22R) (SEQ ID NO:5).

20. A method of treating Alzheimer's in a mammal, comprising administering an effective amount of a dendritic cell to the mammal, wherein the dendritic cell has been pulsed with a peptide comprising an amino acid sequence selected from among DAEFRHDSGYEVHHQKLVFFAWDVGSNKGAIIGLMVGGVVIA (Amyloid beta mutant P22W) (SEQ ID NO:1), DAEFRHDSGYEVHHQKLVFFAEDMGSNKGAIIGLMVGGVVIA (Amyloid beta mutant P24M) (SEQ ID NO:2), DAEFRHDSGYEVHHQKLVFFAEDGGSNKGAIIGLMVGGVVIA (Amyloid beta mutant P24G) (SEQ ID NO:3), DAEFRHDSGYEVHHQKLVFFAFDVGSNKGAIIGLMVGGVVIA (Amyloid beta mutant P22F) (SEQ ID NO:4), or DAEFRHDSGYEVHHQKLVFFARDVGSNKGAIIGLMVGGVVIA (Amyloid beta mutant P22R) (SEQ ID NO:5).

21. The method of claim 19, wherein said peptide consists of an amino acid sequence selected from among DAEFRHDSGYEVHHQKLVFFAWDVGSNKGAI- IGLMVGGVVIA (Amyloid beta mutant P22W) (SEQ ID NO:1), or DAEFRHDSGYEVHHQKLVFFAEDMGSNK-GAIIGLMVGGVVIA (Amyloid beta mutant P24M) (SEQ ID NO:2), or DAEFRHDSGYEVHHQKLVF-FAEDGGSNKGAIIGLMVGGVVIA (Amyloid beta mutant P24G) (SEQ ID NO:3), or DAEFRHDSGYEVHHQKLVF-FAFDVGSNKGAIIGLMVGGVVIA (Amyloid beta mutant P22F) (SEQ ID NO:4), or DAEFRHDSGYEVHHQKLVF-FARDVGSNKGAIIGLMVGGVVIA (Amyloid beta mutant P22R) (SEQ ID NO:5).

22. The method of claim 20, wherein said peptide consists of an amino acid sequence DAEFRHDSGYEVHHQKLVF-FAWDVGSNKGAIIGLMVGGVVIA (Amyloid beta mutant P22W) (SEQ ID NO:1), or DAEFRHDSGYEVHHQKLVF-FAEDMGSNKGAIIGLMVGGVVIA (Amyloid beta mutant P24M) (SEQ ID NO:2), or DAEFRHDSGYEVHHQKLVF-FAEDGGSNKGAIIGLMVGGVVIA (Amyloid beta mutant P240) (SEQ ID NO:3), or DAEFRHDSGYEVHHQKLVF-FAFDVGSNKGAIIGLMVGGVVIA (Amyloid beta mutant P22F) (SEQ ID NO:4), or DAEFRHDSGYEVHHQKLVF-FARDVGSNKGAIIGLMVGGVVIA (Amyloid beta mutant P22R) (SEQ ID NO:5).

* * * * *

UNITED STATES PATENT AND TRADEMARK OFFICE

CERTIFICATE OF CORRECTION

PATENT NO. : 8,188,046 B2
APPLICATION NO. : 12/444647
DATED : May 29, 2012
INVENTOR(S) : Chuanhai Cao It is certified that error appears in the above-identified patent and that said Letters Patent is hereby corrected as shown below:

Column 3,
Lines 63-64, "DAEFRIIDSGYE" should read --DAEFRHDSGYE--.

Column 8,
Line 58, "Glutamine (Gin)" should read --Glutamine (Gln)--.

Column 11, table 1,
Line 3, "andH LA" should read --and HLA--.

Column 11, table 1, column 3,
Lines 5-6, "Antigenic Comain" should read --Antigenic Domain--.

Column 12,
Line 7, "levels from blood taken" should read --levels, blood was taken--.
Line 8, "phlebotomy under restrained" should read --phlebotomy under restraint--.
Line 63, "the Bio-Plea system" should read --the Bio-Plex system--.

Column 13,
Line 24, "antibody level (FIG.1)" should read --antibody levels are shown in FIG. 1--.

Columns 13-14, table 2, column 2,
Line 8, "DAEFRHDSGYFVHH" should read --DAEFRHDSGYEVHH--.

Column 14,
Line 17, "is highly homology among" should read --is highly homologous among--.

Columns 15-16, table 2, column 2,
Line 3, "KLVFEAE" should read --KLVFFAE--.

Signed and Sealed this
Twenty-seventh Day of November, 2012

David J. Kappos
*Director of the United States Patent and Trademark Office*

Column 15, table 3, column 2,
Line 27, "KLVEFA" should read --KLVFFA--.

Column 16,
Lines 36-37, "TNF-a" should read --TNF-α--.

Column 31, claim 1,
Line 56, "or DAEFRIIDSG" should read --or DAEFRHDSG--.

Column 36, claim 22,
Line 6, "P240)" should read --P24G)--.